(12) United States Patent
Jackson et al.

(10) Patent No.: US 12,419,718 B2
(45) Date of Patent: Sep. 23, 2025

(54) ABSORBENT LINER, SYSTEMS AND METHODS OF USE

(71) Applicant: Medivators Inc., Minneapolis, MN (US)

(72) Inventors: Mark Jackson, Great Wakering (GB); Joshua J. Korth, St. Louis Park, MN (US); Gary Spencer, Rayleigh (GB); Stephen Nichols, Witham (GB)

(73) Assignee: Medivators Inc., Minneapolis, MN (US)

( * ) Notice: Subject to any disclaimer, the term of this patent is extended or adjusted under 35 U.S.C. 154(b) by 902 days.

(21) Appl. No.: 17/618,987

(22) PCT Filed: Jun. 8, 2020

(86) PCT No.: PCT/US2020/036630
§ 371 (c)(1),
(2) Date: Dec. 14, 2021

(87) PCT Pub. No.: WO2020/256989
PCT Pub. Date: Dec. 24, 2020

(65) Prior Publication Data
US 2022/0304764 A1 Sep. 29, 2022

Related U.S. Application Data

(60) Provisional application No. 62/864,115, filed on Jun. 20, 2019.

(51) Int. Cl.
*A61B 50/39* (2016.01)
*A61B 50/33* (2016.01)
(Continued)

(52) U.S. Cl.
CPC .............. *A61B 50/39* (2016.02); *A61B 50/33* (2016.02); *A61B 90/70* (2016.02); *A61L 2/07* (2013.01);
(Continued)

(58) Field of Classification Search
CPC ........ A61B 2050/3006; A61B 1/00144; A61B 50/33; A61B 50/39; A61B 2090/701
(Continued)

(56) References Cited

U.S. PATENT DOCUMENTS 803,102 A 10/1905 Harris
1,592,726 A 7/1926 Dunbar
(Continued)

FOREIGN PATENT DOCUMENTS

CN 108030556 A 5/2018
DE 202016105248 12/2016
(Continued)

OTHER PUBLICATIONS

ARES flexible endoscope automated reprocessing system' (Steelco) Jul. 12, 2018 (Jul. 12, 2018) [retrieved from the internet on Aug. 24, 2020 (Aug. 24, 2020) at https://web.archive.org/web/20180712214831/http://www.peacocks.net/_filecache/9e4/a6e/550-steelco-ares-rev04.pdf].
(Continued)

*Primary Examiner* — Ernesto A Grano

(57) ABSTRACT

A liner for an endoscope storage tray is provided. The liner has an interior comprising a flexibly deformable material substantially impermeable to fluids and an absorbent material disposed within or attached to at least a portion of the flexibly deformable material. The liner is configured to temporarily line at least an interior of the endoscope storage tray. Systems and methods are also provided.

9 Claims, 18 Drawing Sheets

(51) Int. Cl.
*A61B 90/70* (2016.01)
*A61L 2/07* (2006.01)
*A61L 2/20* (2006.01)
*A61L 2/26* (2006.01)
*A61B 50/30* (2016.01)

(52) U.S. Cl.
CPC .............. *A61L 2/206* (2013.01); *A61L 2/26* (2013.01); *A61B 2050/3014* (2016.02); *A61B 2050/314* (2016.02); *A61B 2090/701* (2016.02); *A61L 2202/181* (2013.01); *A61L 2202/23* (2013.01)

(58) Field of Classification Search
USPC ........................................................ 206/363
See application file for complete search history.

(56) References Cited

U.S. PATENT DOCUMENTS

| | | | |
|---|---|---|---|
| 1,717,974 | A | 6/1929 | Heinrichs |
| 2,080,108 | A | 5/1937 | Bradstein |
| 2,214,946 | A | 9/1940 | Werner |
| 2,412,325 | A | 12/1946 | Devine et al. |
| 3,157,902 | A | 11/1964 | Hardwick |
| 3,757,990 | A | 9/1973 | Buth |
| 3,770,119 | A | 11/1973 | Hultberg et al. |
| 3,949,934 | A | 4/1976 | Goglio |
| 4,042,109 | A | 8/1977 | Barcan |
| 4,053,280 | A | 10/1977 | Salisbury |
| 4,256,225 | A | 3/1981 | Jackson |
| 4,466,552 | A | 8/1984 | Butterworth et al. |
| 4,574,978 | A | 3/1986 | Hodges |
| 4,583,643 | A | 4/1986 | Sanderson |
| 4,704,254 | A | 11/1987 | Nichols |
| 4,730,729 | A | 3/1988 | Harry |
| 4,750,619 | A | 6/1988 | Cohen et al. |
| 4,754,595 | A | 7/1988 | Sanderson |
| 4,903,718 | A | 2/1990 | Sullivan |
| 4,948,266 | A | 8/1990 | Bencic |
| 5,108,195 | A | 4/1992 | Perron |
| 5,207,325 | A | 5/1993 | Kennedy |
| 5,263,777 | A | 11/1993 | Domke |
| 5,288,467 | A | 2/1994 | Biermaier |
| 5,295,606 | A | 3/1994 | Karwoski |
| 5,392,917 | A | 2/1995 | Alpern et al. |
| 5,409,126 | A | 4/1995 | Demars |
| 5,443,801 | A | 8/1995 | Langford |
| 5,733,243 | A | 3/1998 | Yabe et al. |
| 5,882,589 | A | 3/1999 | Mariotti |
| 5,989,608 | A | 11/1999 | Mizuno |
| 6,029,844 | A | 2/2000 | Brady |
| 6,041,794 | A | 3/2000 | Lin et al. |
| 6,139,185 | A | 10/2000 | Hamilton et al. |
| 6,151,910 | A | 11/2000 | Hazen |
| 6,235,692 | B1 | 5/2001 | Scoville et al. |
| 6,305,567 | B1 | 10/2001 | Sulpizio |
| 6,312,645 | B1 | 11/2001 | Lin et al. |
| 6,378,721 | B1 | 4/2002 | Williams |
| 6,380,524 | B1 | 4/2002 | Keller |
| 6,622,862 | B1 | 9/2003 | Corrado |
| 6,622,864 | B1 | 9/2003 | Debbs et al. |
| 6,641,781 | B2 | 11/2003 | Walta |
| 6,733,803 | B1 | 5/2004 | Karsten |
| 6,749,063 | B2 | 6/2004 | Parker |
| 6,916,456 | B2 | 7/2005 | Martineau et al. |
| 6,994,823 | B2 | 2/2006 | Hight, III |
| 7,041,941 | B2 | 5/2006 | Faries, Jr. et al. |
| D531,734 | S | 11/2006 | Haunschild et al. |
| 7,132,089 | B2 | 11/2006 | Lacabanne |
| 7,178,555 | B2 | 2/2007 | Engel et al. |
| 7,476,368 | B2 | 1/2009 | Sargent et al. |
| 7,630,791 | B2 | 12/2009 | Nguyen et al. |
| 7,993,602 | B2 | 8/2011 | Moriyama et al. |
| 8,287,816 | B2 | 10/2012 | Kral |
| 8,414,471 | B2 | 4/2013 | Mandava et al. |
| 8,435,445 | B2 | 5/2013 | Kral |
| 8,454,901 | B1 | 6/2013 | Snyder, III |
| 8,733,551 | B2 | 5/2014 | Parker et al. |
| 8,795,603 | B2 | 8/2014 | Ghelman et al. |
| 8,851,287 | B2 | 10/2014 | Becklin |
| 8,905,258 | B2 | 12/2014 | Javid et al. |
| 9,348,013 | B2 | 5/2016 | Rahim et al. |
| 9,703,264 | B2 | 7/2017 | Freijsen et al. |
| 9,910,965 | B2 | 3/2018 | Bufalini et al. |
| D818,841 | S | 5/2018 | Newton |
| D819,409 | S | 6/2018 | Newton |
| 10,405,938 | B2 | 9/2019 | Ramsey |
| 10,418,831 | B2 | 9/2019 | Racenet et al. |
| 10,456,494 | B2 | 10/2019 | Roudebush et al. |
| 10,463,441 | B2 | 11/2019 | Tate et al. |
| D909,883 | S | 2/2021 | Newton |
| D921,490 | S | 6/2021 | Newton |
| 11,445,900 | B2 * | 9/2022 | King ................. A61B 1/125 |
| 11,696,811 | B2 * | 7/2023 | Dalena ............... A61B 50/33 |
| | | | 206/363 |
| 2003/0078472 | A1 | 4/2003 | Parker |
| 2004/0101456 | A1 | 5/2004 | Kuroshima et al. |
| 2005/0000553 | A1 * | 1/2005 | Noguchi ............. A61B 1/125 |
| | | | 134/84 |
| 2005/0260097 | A1 | 11/2005 | Williams et al. |
| 2006/0193761 | A1 | 8/2006 | Moriyama et al. |
| 2007/0215507 | A1 | 9/2007 | Glenn et al. |
| 2007/0228080 | A1 | 10/2007 | Lin et al. |
| 2008/0251102 | A1 | 10/2008 | Haack et al. |
| 2009/0091453 | A1 | 4/2009 | Ishida et al. |
| 2009/0104094 | A1 | 4/2009 | Affaitati |
| 2009/0123333 | A1 | 5/2009 | Parker et al. |
| 2009/0206674 | A1 | 8/2009 | Noguchi et al. |
| 2010/0176016 | A1 | 7/2010 | Pell |
| 2010/0189598 | A1 | 7/2010 | Fraundorfer |
| 2011/0002811 | A1 | 1/2011 | Dane et al. |
| 2011/0192744 | A1 | 8/2011 | Parker et al. |
| 2012/0152289 | A1 | 6/2012 | Smith et al. |
| 2013/0019910 | A1 | 1/2013 | Ledel |
| 2013/0105344 | A1 | 5/2013 | Hartley |
| 2013/0192647 | A1 | 8/2013 | Ledel et al. |
| 2014/0069841 | A1 | 3/2014 | Pizzato et al. |
| 2014/0083886 | A1 | 3/2014 | Winterrowd et al. |
| 2014/0182629 | A1 | 7/2014 | Dromard et al. |
| 2014/0270583 | A1 | 9/2014 | Anderson |
| 2014/0339114 | A1 | 11/2014 | Griffin |
| 2014/0353203 | A1 | 12/2014 | Hu et al. |
| 2015/0257632 | A1 * | 9/2015 | Ramsey ............. B65D 81/267 |
| | | | 206/204 |
| 2015/0259122 | A1 | 9/2015 | Parker |
| 2015/0272680 | A1 | 10/2015 | Suzuki |
| 2016/0058900 | A1 | 3/2016 | Sato |
| 2016/0081540 | A1 | 3/2016 | Suzuki |
| 2016/0095508 | A1 | 4/2016 | Terliuc et al. |
| 2016/0249915 | A1 | 9/2016 | Beckman et al. |
| 2017/0056122 | A1 * | 3/2017 | Ramsey ............... A61B 50/36 |
| 2017/0091389 | A1 | 3/2017 | Dukatz |
| 2017/0172397 | A1 * | 6/2017 | Zardini ............... A61B 1/125 |
| 2018/0028703 | A1 | 2/2018 | McLaughlin et al. |
| 2018/0071045 | A1 | 3/2018 | Cohen et al. |
| 2018/0134453 | A1 | 5/2018 | Wassenburg |
| 2019/0021806 | A1 | 1/2019 | Turbett |
| 2019/0365500 | A1 | 12/2019 | Erdmann et al. |
| 2019/0388181 | A1 * | 12/2019 | Petersen ............... A46B 9/026 |
| 2020/0118674 | A1 | 4/2020 | Le et al. |
| 2020/0187767 | A1 * | 6/2020 | Kramer ............... A61B 1/123 |
| 2020/0205925 | A1 * | 7/2020 | Cummings ........... A61B 50/30 |
| 2020/0315731 | A1 | 10/2020 | Zardini et al. |
| 2021/0023250 | A1 * | 1/2021 | Golkowski ............. C01B 15/01 |
| 2021/0076923 | A1 | 3/2021 | Awau |
| 2021/0128768 | A1 | 5/2021 | Jackson et al. |
| 2021/0138517 | A1 * | 5/2021 | Kakar ................. B08B 3/047 |
| 2021/0186641 | A1 | 6/2021 | Cummings et al. |
| 2021/0187141 | A1 | 6/2021 | Crotti |
| 2021/0212796 | A1 | 7/2021 | Crotti |
| 2021/0356051 | A1 | 11/2021 | Gray-Dreizler et al. |
| 2022/0195334 | A1 * | 6/2022 | Bui .................... C11D 7/264 |
| 2022/0211458 | A1 * | 7/2022 | Jackson ............... A61B 50/33 |

(56) References Cited

U.S. PATENT DOCUMENTS

| | | | |
|---|---|---|---|
| 2022/0304560 A1* | 9/2022 | Jackson | A61B 1/00131 |
| 2022/0304762 A1* | 9/2022 | Jackson | A61B 50/33 |
| 2022/0304764 A1 | 9/2022 | Jackson et al. | |
| 2022/0387651 A1 | 12/2022 | Kendrick | |
| 2022/0392102 A1 | 12/2022 | Ohara et al. | |
| 2023/0082582 A1* | 3/2023 | Jackson | A61B 50/33 206/363 |
| 2023/0285614 A1 | 9/2023 | Kotani et al. | |
| 2024/0050181 A1* | 2/2024 | Aehlig | A61B 50/36 |

FOREIGN PATENT DOCUMENTS

| | | | |
|---|---|---|---|
| EP | 0091792 B1 | | 1/1988 |
| EP | 0830295 | A1 | 3/1998 |
| EP | 2689706 | A2 | 1/2014 |
| EP | 2900117 | A1 | 8/2015 |
| JP | 2007054343 | | 3/2007 |
| JP | 2009172228 | | 8/2009 |
| JP | 2008054861 | | 3/2020 |
| WO | 9607364 | | 3/1996 |
| WO | 2011151641 | | 12/2011 |
| WO | 2018024690 | | 2/2018 |
| WO | 2018152400 | A1 | 8/2018 |

OTHER PUBLICATIONS

International Preliminary Report on Patentability dated Dec. 30, 2021, of International PCT Application No. PCT/US/2020/036618 dated Jun. 8, 2020.

International Search Report and Written Opinion of the International Searching Authority Dated Sep. 9, 2020, of International PCT Application No. PCT/US2020/036618 filed Jun. 8, 2020.

Steelco ED200 Endoscope Drying/Storage Cabinet' (Peacocks Medical Group) Jun. 20, 2018(Jun. 28, 2018) [retreived from the internet on Aug. 24, 2020 (Aug. 24, 2020) at https://web.archive.org/web/20180620034054/https://www.peacocks.net/medical-decontamination/endoscopy/endoscopy-drying-cabinetslsteelco-ed200.

International Preliminary Report on Patentability dated Dec. 30, 2021, of International PCT Application No. PCT/US/2020/036630 dated Jun. 8, 2020.

International Preliminary Report on Patentability dated Dec. 30, 2021, of International PCT Application No. PCT/US/2020/036635 dated Jun. 8, 2020.

International Preliminary Report on Patentability dated Sep. 9, 2022 of International PCT Application No. PCT/US/2021/018463 dated Feb. 18, 2021.

International Preliminary Report on Patentability dated Sep. 30, 2021, of International PCT Application No. PCT/US2020/019640, dated Feb. 25, 2020.

International Search Report and Written Opinion mailed May 6, 2021, in International Application No. PCT/US2021/018463 filed Feb. 18, 2021.

International Search Report and Written Opinion mailed Nov. 20, 2020, in International Application No. PCT/US2020/036635 filed Jun. 8, 2020.

International Search Report and Written Opinion of the International Searching Authority Dated Jun. 5, 2020, of International PCT Application No. PCT/US2020/019640 filed Feb. 25, 2020.

International Search Report and Written Opinion of the International Searching Authority Dated Sep. 3, 2020, of International PCT Application No. PCT/US2020/036630 filed Jun. 8, 2020.

* cited by examiner

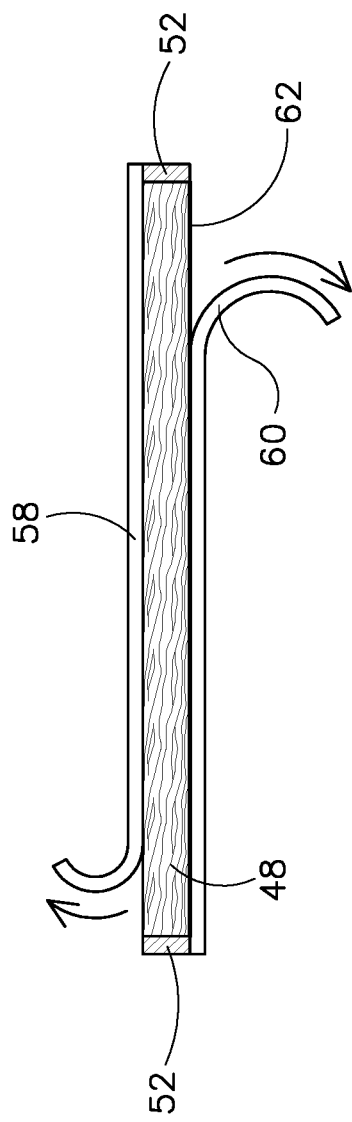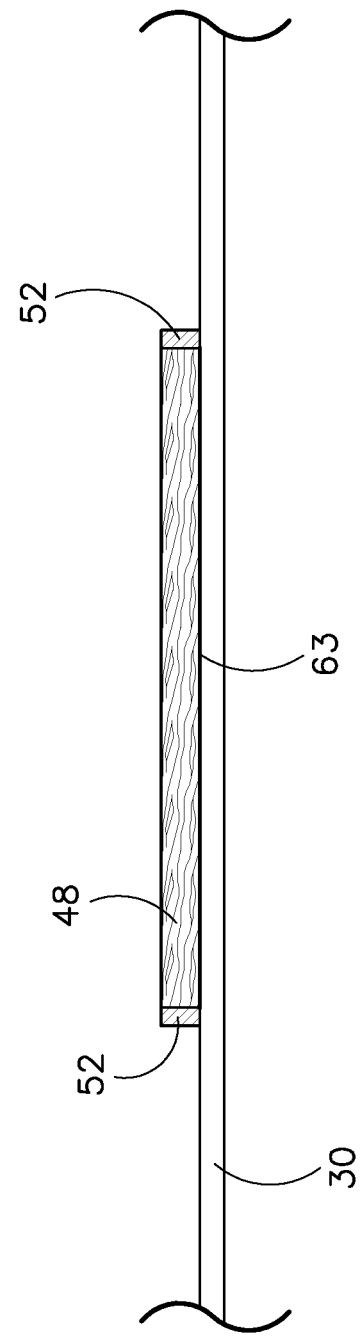
FIG. 6A
FIG. 6B

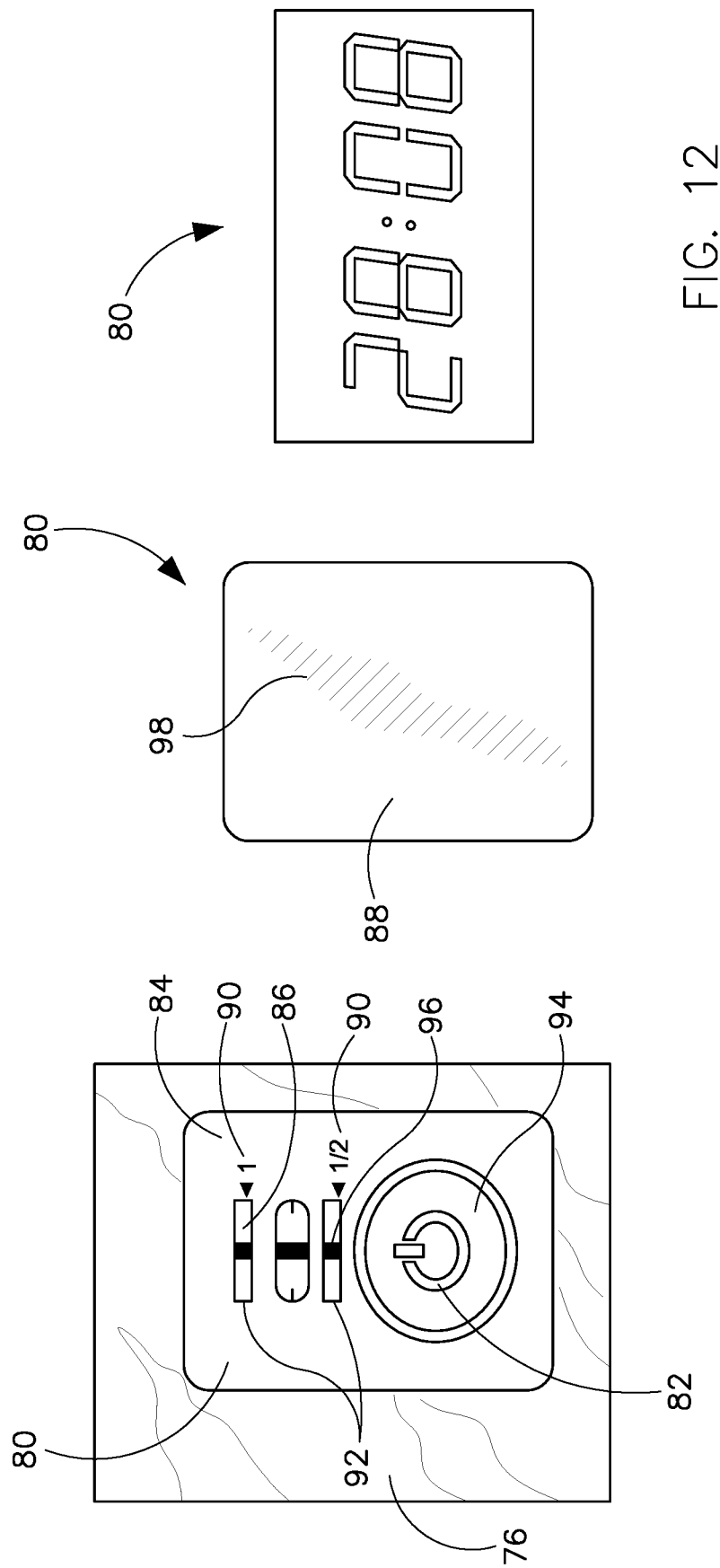

ABSORBENT LINER, SYSTEMS AND METHODS OF USE

PRIORITY CLAIM

This application claims priority to and the benefit of U.S. Provisional application with Ser. No. 62/864,115, filed on Jun. 20, 2019, entitled ABSORBENT LINER, SYSTEMS AND METHODS OF USE, which is herein incorporated by reference in its entirety.

BACKGROUND

Endoscopes are well-known in the art and are commonly used for numerous medical procedures. After each use, an endoscope will be sent to a decontamination room and will undergo reprocessing. Reprocessing of the endoscope cleans, disinfects and/or sterilizes to reduce or prevent contaminants from settling onto the endoscope, as well as to prevent the spread of disease, viruses, bacteria, and illness.

After endoscope reprocessing and drying to remove moisture from the exterior surface of the endoscope and its channels, an endoscope is generally disposed within a tray and a cover can be secured to the perimeter of the tray. The tray can then be loaded into a cart. The endoscope is then transported to a procedure room ready for use.

Sometimes a contaminated or used endoscope cannot be transported to the decontamination room for reprocessing in a timely manner. For example, if an endoscopy is performed on a weekend or late at night, the contaminated endoscope may not be sent to the decontamination room on time due to it being a weekend or late at night. As a result, the endoscope can remain contaminated with body fluids which can create a contamination risk and may result in adherent material or the formation of a biofilm on the endoscope. The biofilm can then dry and be difficult to remove from the endoscope. It would be beneficial to prevent adherent material or the biofilm on the endoscope from drying on the endoscope including its working channels as these are difficult to clean especially when the biofilm dries.

There is a need to develop a liner for an endoscope storage tray that includes an absorbent material that is contacted with a fluid to provide a moist environment for a contaminated endoscope while it is stored in the tray until the endoscope can be reprocessed. There is also a need for a liner that includes an absorbent base configured to contact a foam detergent to keep the endoscope and its channels moist. Further, there is a need to provide a timing mechanism that can be used to determine the period of time that has lapsed since the contaminated endoscope has been used in a procedure.

SUMMARY

New devices, systems and methods are provided that create a moist environment for a contaminated endoscope and its inner channels while the endoscope is stored for reprocessing.

In some embodiments, a liner for an endoscope storage tray is provided. The liner has an interior comprising a flexibly deformable material substantially impermeable to fluids and an absorbent material disposed within or attached to at least a portion of the flexibly deformable material. The liner is configured to temporarily line at least an interior of the endoscope storage tray.

In some embodiments, an endoscope storage system is provided. The system comprises a cover for an endoscope storage tray. The cover comprises a flexibly deformable sheet material substantially impermeable to fluids. The flexibly deformable sheet material is configured to be temporarily secured to the endoscope storage tray so as to cover at least an interior of the endoscope storage tray. A liner is provided having an interior comprising a flexibly deformable material substantially impermeable to fluids, and an absorbent material is disposed within or attached to at least a portion of the flexibly deformable material of the liner. The liner is configured to temporarily line at least the interior of the endoscope storage tray.

In some embodiments, an endoscope storage system is provided. The system comprises a cover for an endoscope storage tray. The cover comprises a flexibly deformable sheet material substantially impermeable to fluids. The flexibly deformable sheet material is configured to be temporarily secured to the endoscope storage tray so as to cover at least an interior of the endoscope storage tray. A liner is provided having an interior comprising a flexibly deformable material substantially impermeable to fluids and an absorbent material disposed within or attached to at least a portion of the flexibly deformable material of the liner. The liner is configured to temporarily line at least the interior of the endoscope storage tray. A detergent container is provided having detergent disposed therein.

An endoscope storage system is provided. The system comprises a cover for an endoscope storage tray comprising a flexibly deformable sheet material substantially impermeable to fluids. The flexibly deformable sheet material is configured to be temporarily secured to the endoscope storage tray so as to cover at least an interior of the endoscope storage tray. A liner is provided having an interior comprising a flexibly deformable material substantially impermeable to fluids and an absorbent material disposed within or attached to at least a portion of the flexibly deformable material of the liner. The liner is configured to temporarily line at least the interior of the endoscope storage tray. A detergent container is provided having an outlet configured to dispense detergent to an inlet of the cover, liner and/or endoscope storage tray and to the interior of the endoscope storage tray.

A method of preventing or reducing contaminants from drying in or on an endoscope is provided. The method comprising disposing the endoscope on a liner, the liner having an interior comprising a flexibly deformable material substantially impermeable to fluids and an absorbent material disposed within or attached to at least a portion of the flexibly deformable material of the liner; and applying a fluid to an exterior surface of the endoscope and interior surfaces of the endoscope and/or the absorbent material of the liner.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE DRAWINGS

In part, other aspects, features, benefits and advantages of the embodiments will be apparent with regard to the following description, appended claims and accompanying drawings.

FIG. 6A illustrates a cross sectional side view of the absorbent material as a separate detachable component of the liner. The plastic removable film of FIG. 5 is shown and a second plastic removable film is shown in contact with a bottom mating surface of the absorbent material. The mating surface can include an adhesive to facilitate attachment to a corresponding mating surface on an existing liner.

FIG. 6B illustrates a cross sectional side view of the absorbent material of FIG. 6A attached to an existing liner.

FIG. 10 illustrates a front view of the timing mechanism of FIG. 8.

FIG. 11 illustrates a back view of the timing mechanism of FIG. 10.

FIG. 12 illustrates a front view of an embodiment of the timing mechanism. In this embodiment, the timing mechanism is digital.

Figure 1:
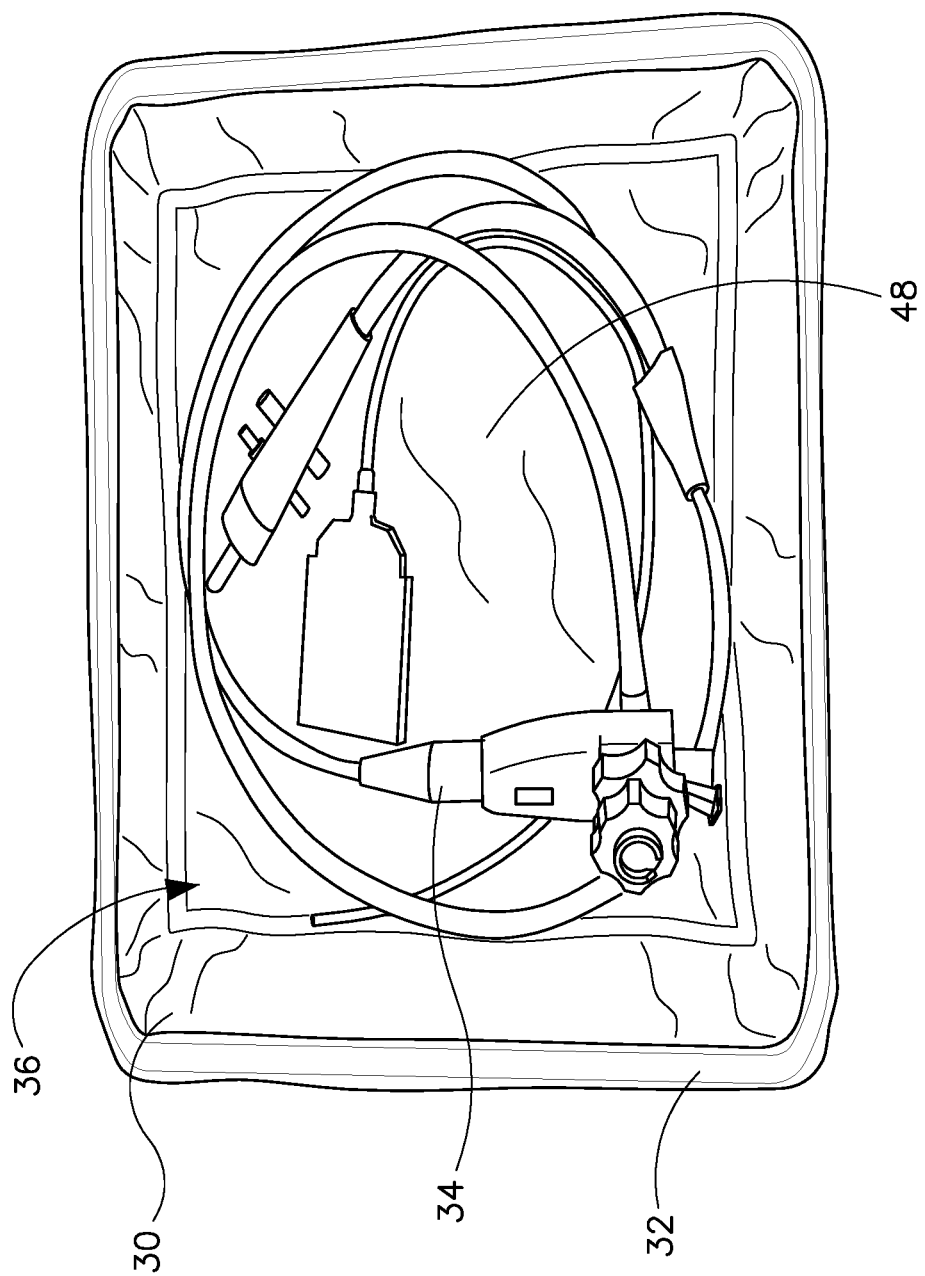
FIG. 1 illustrates a perspective view of a liner, an endoscope storage tray and an endoscope. The liner includes an interior comprising a flexibly deformable material substantially impermeable to fluids and an absorbent material disposed within or attached to at least a portion of the flexibly deformable material. The liner is configured to temporarily line at least an interior of the endoscope storage tray.

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding the numerical ranges and parameters set forth herein, the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents that may be included within the invention as defined by the appended claims.

It is noted that, as used in this specification and the appended claims, the singular forms "a," "an," and "the," include plural referents unless expressly and unequivocally limited to one referent. Thus, for example, reference to "outlet" includes one, two, three or more outlets.

We refer now to the drawings wherein depicted elements are not necessarily shown to scale and wherein like or similar elements are designated by the same reference numeral through the several views.

Referring to the drawings in general, it will be understood that the illustrations are for the purpose of describing particular embodiments of the disclosure and are not intended to be limiting thereto.

While most of the terms used herein will be recognizable to those of ordinary skill in the art, it should be understood that when not explicitly defined, terms should be interpreted as adopting a meaning presently accepted by those of ordinary skill in the art.

Liner

New devices, systems and methods are provided that create a moist environment for a contaminated endoscope and its inner channels while the endoscope is stored and waiting to be reprocessed.

In some embodiments, a liner for an endoscope storage tray is provided. The liner has an interior comprising a flexibly deformable material substantially impermeable to fluids and an absorbent material disposed within or attached to at least a portion of the flexibly deformable material. The liner is configured to temporarily line at least an interior of the endoscope storage tray.

Referring to FIGS. 1-6B, a liner 30 for an endoscope storage tray 32 is provided. The liner is configured to facilitate a moist environment for an endoscope 34 stored in the tray. The endoscope can be a contaminated endoscope that is a contamination risk and/or has biofilm formed on and/or within the endoscope channels. The liner can reduce or prevent the biofilm and other contaminants from drying which can cause blockage in one or more endoscope channels or the dried biofilm can be difficult to clean and remove from the endoscope. The liner is configured to engage with the tray by temporarily lining at least an interior 36 of the endoscope tray, as described herein. The liner can be a sterile or non-sterile disposable liner.

Figure 2:
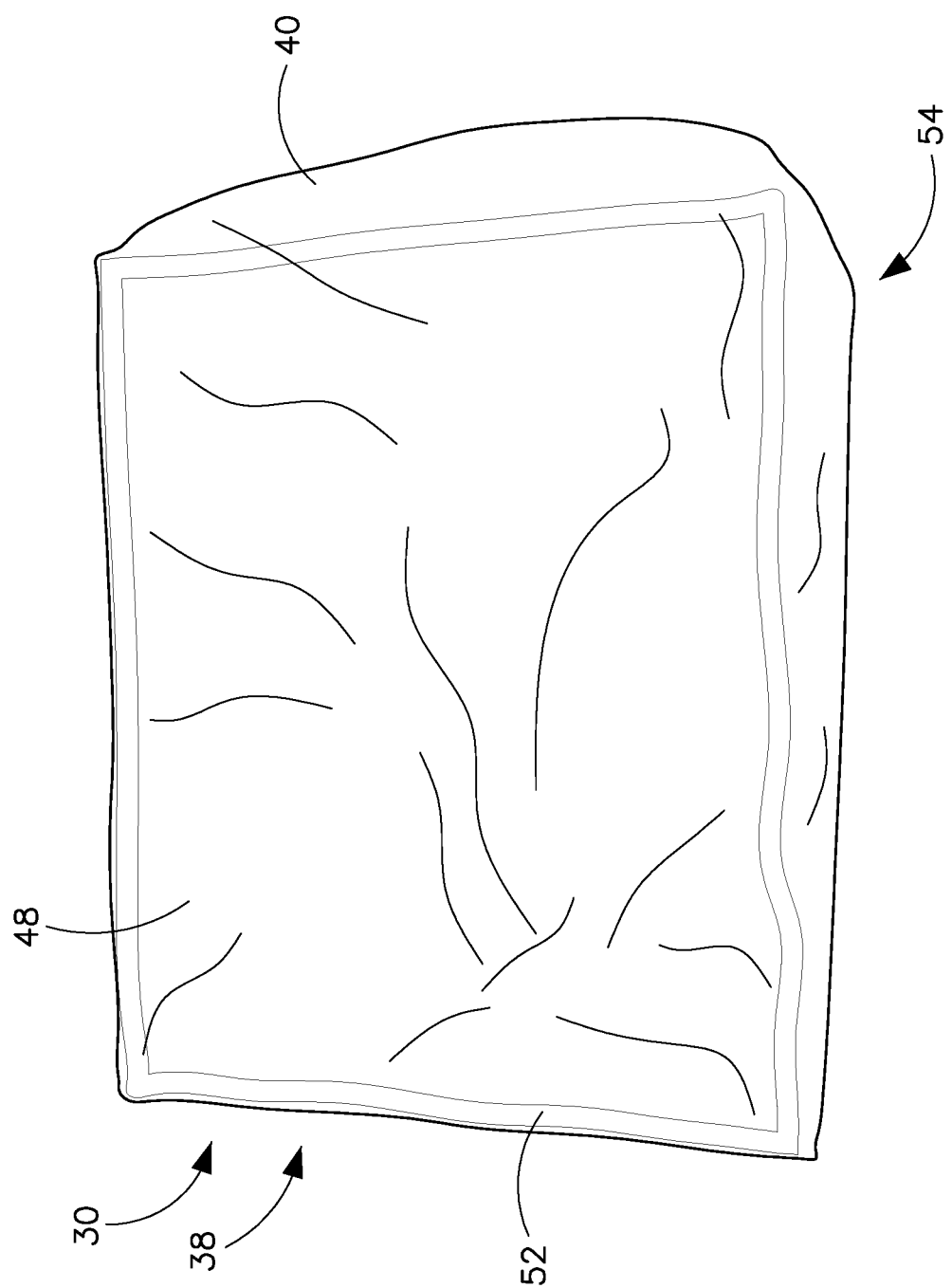
FIG. 2 illustrates a perspective view of the liner shown in FIG. 1.

The liner includes an interior 38 that defines a flexibly deformable material 40, as shown in FIG. 2. The flexibly deformable material is substantially impermeable to fluids so as to prevent fluid from permeating through the liner and into the tray. Flexibly deformable is defined relative to the rigid tray, where the material is capable of being movable, bendable and/or moldable such that the material can be reshaped, stretched and/or manipulated. Substantially impermeable is defined as a material that is almost entirely impenetrable to fluids, preventing most fluids from passing through the material. In some embodiments, the flexibly deformable material is substantially impermeable or is entirely impermeable to fluids and/or air.

Figure 3:
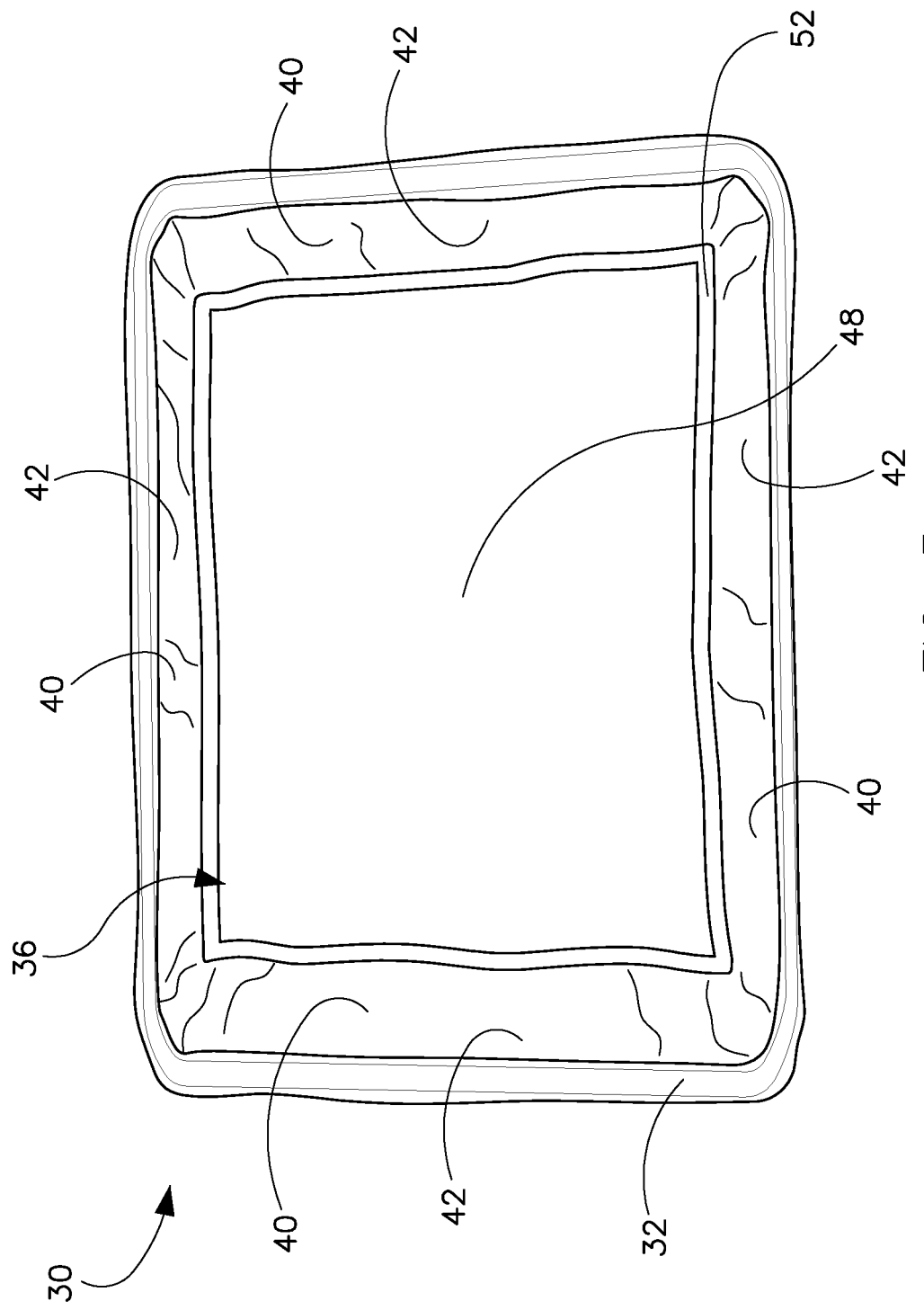
FIG. 3 illustrates a perspective view of the liner of FIG. 1 disposed with the tray of FIG. 1.

The flexibly deformable material can engage with portions of the interior of the tray, surrounding sidewalls 42, a rim 44 and/or a peripheral lip 46 of the tray, as shown in FIGS. 1 and 3. For example, portions of the deformable material can entirely cover the surrounding sidewalls of the tray and extend over the rim and/or the rim and the lip of the tray.

The flexibly deformable material can have a certain thickness from about 1 mm to about 8 mm. In some embodiments, the thickness of the flexibly deformable material can be from about 1, 2, 3, 4, 5, 6, 7 to about 8 mm.

The flexibly deformable material can be non-porous and/or be made from a hydrophobic material or a hydrophobic coating can be applied to the flexibly deformable material. The flexibly deformable material can be made from a tightly woven synthetic and/or non-synthetic material. It is contemplated that the flexibly deformable material can be durable and tear-resistant. The flexibly deformable material can be made from polyethylene and/or high density polythene (HDP).

The flexibly deformable material can comprise from about 20 to about 70 percent of the liner. In some embodiments, the flexibly deformable material can comprise from about 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69 to about 70 percent of the liner.

The interior of the liner defines an absorbent material 48 that is disposed within or attached to at least a portion of the flexibly deformable material, as shown in FIG. 2. In some embodiments, the absorbent material is configured to contact and/or retain a fluid, as described herein, to provide the moist environment for the endoscope stored in the tray. The absorbent material can also be configured to conform to a bottom surface 50 of the interior of the tray.

The absorbent material can be attached to the liner by an adhesive, heat sealed, stitching and/or welding. In some embodiments, the absorbent material and the flexibly deformable material are monolithic. The absorbent material can be integral with the portion of the flexibly deformable material of the liner.

A perimeter 52 can be defined by the absorbent material and the perimeter attaches to the flexibly deformable material of the liner, as shown in FIGS. 3-7. The perimeter can be made from the same or different material that the absorbent material or the flexibly deformable material is made from. The perimeter can be made of a plastic that is impermeable or substantially impermeable to fluids. A certain thickness can be selected for the perimeter from about 2 mm to about 10 mm. In some embodiments, the thickness of the perimeter can be from about 2, 3, 4, 5, 6, 7, 8, 9 to about 10 mm. The perimeter can have a thickness that is greater than the thickness of the flexibly deformable material. The perimeter can be shaped in a square, rectangular, triangular, oval, regular or irregular shape.

The perimeter can comprise from about 1 to about 10 percent of the liner. In some embodiments, the perimeter can comprise from about 1, 2, 3, 4, 5, 6, 7, 8, 9 to about 10 percent of the liner.

The absorbent material can comprise from about 30 to about 80 percent of the liner. In some embodiments, the absorbent material can comprise from about 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79 to about 80 percent of the liner.

The absorbent material can have a certain thickness from about 2 mm to about 10 mm. In some embodiments, the thickness of the absorbent material can be from about 2, 3, 4, 5, 6, 7, 8, 9 to about 10 mm. The thickness of the absorbent material can be greater than the thickness of the flexibly deformable material and the perimeter. However, the thickness of the perimeter can be equal to, less than or greater than the absorbent material.

The absorbent material can be a sponge material. The sponge material can be made of cellulose, wood fiber, foamed plastic polymer, polyester or a combination thereof. The sponge can be porous and the pores can be tightly packed, loose, configured in discrete regions or randomly disposed within the sponge. The pores can be the same of different sizes and can be from about 1 to about 500 microns. The size of the pores can be from about 1, 2, 3, 4, 5, 6, 7, 8, 9, 10, 11, 12, 13, 14, 15, 16, 17, 18, 19, 20, 30, 40, 50, 60, 70, 80, 90, 100, 120, 140, 160, 180, 200, 220, 240, 260, 280, 300, 320, 340, 360, 380, 400, 420, 440, 460, 480 to about 500 microns.

The absorbent material can be made from a gel, cotton, cellulose, rayon, polyester, hemp, bamboo, microfiber, poly (lactic acid), polyurethane or a combination thereof, and the material can be made from 1 to about 100% of these materials. The material can also be hydrophilic. The absorbent material can also be made from a silicone elastomer, silicone gel, a silicone interpenetrating polymer network or a combination thereof. Interpenetrating polymer networks can include a blend of two or more polymers where each material forms a continuous network, each network interpenetrating the other. The absorbent material can be fibrous and can be woven, non-woven, mesh, a lattice. The absorbent liner can also be multilayered with one or more of the materials described above and can include from about 1, 2, 3, 4, 5, 6, 7, 8, 9 to about 10 layers.

Figure 4:
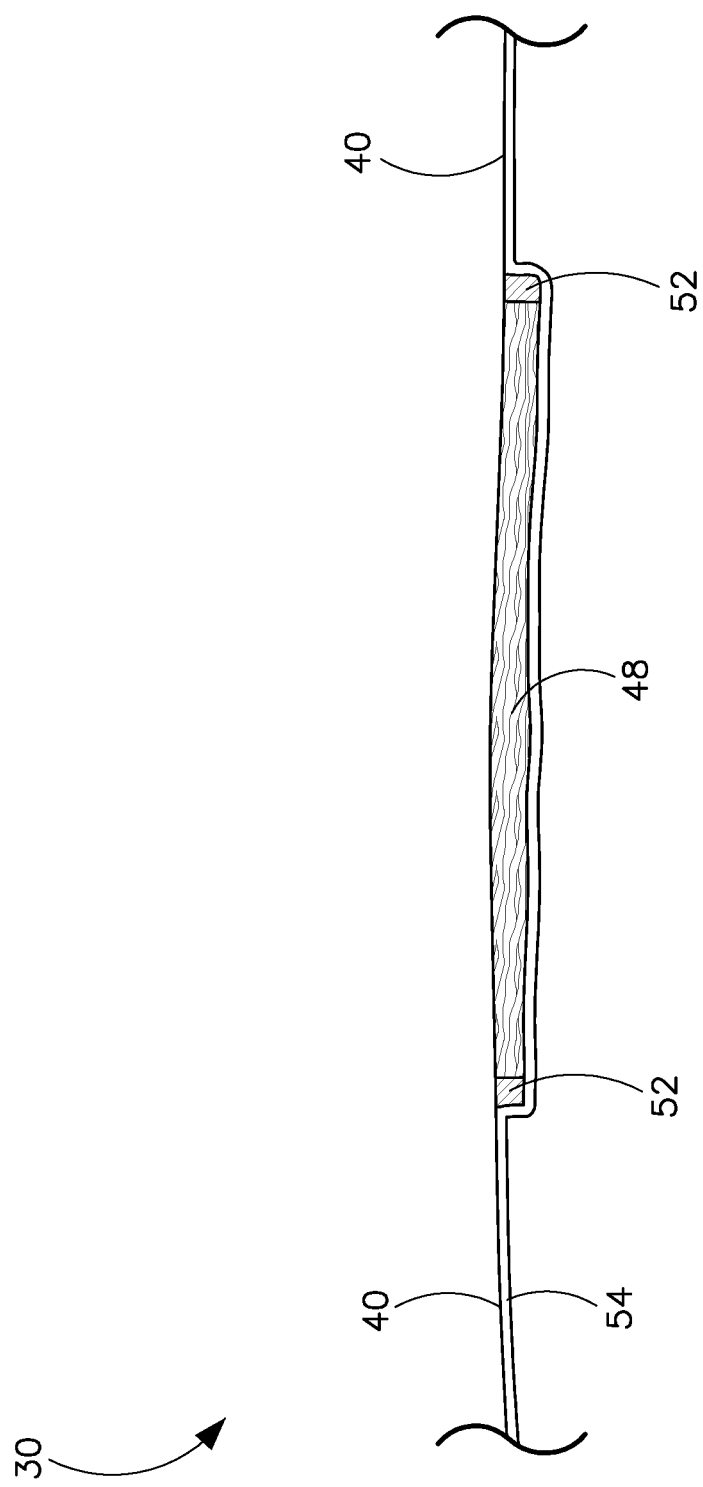
FIG. 4 illustrates a cross sectional side view of the liner of FIG. 1.
Figure 5:
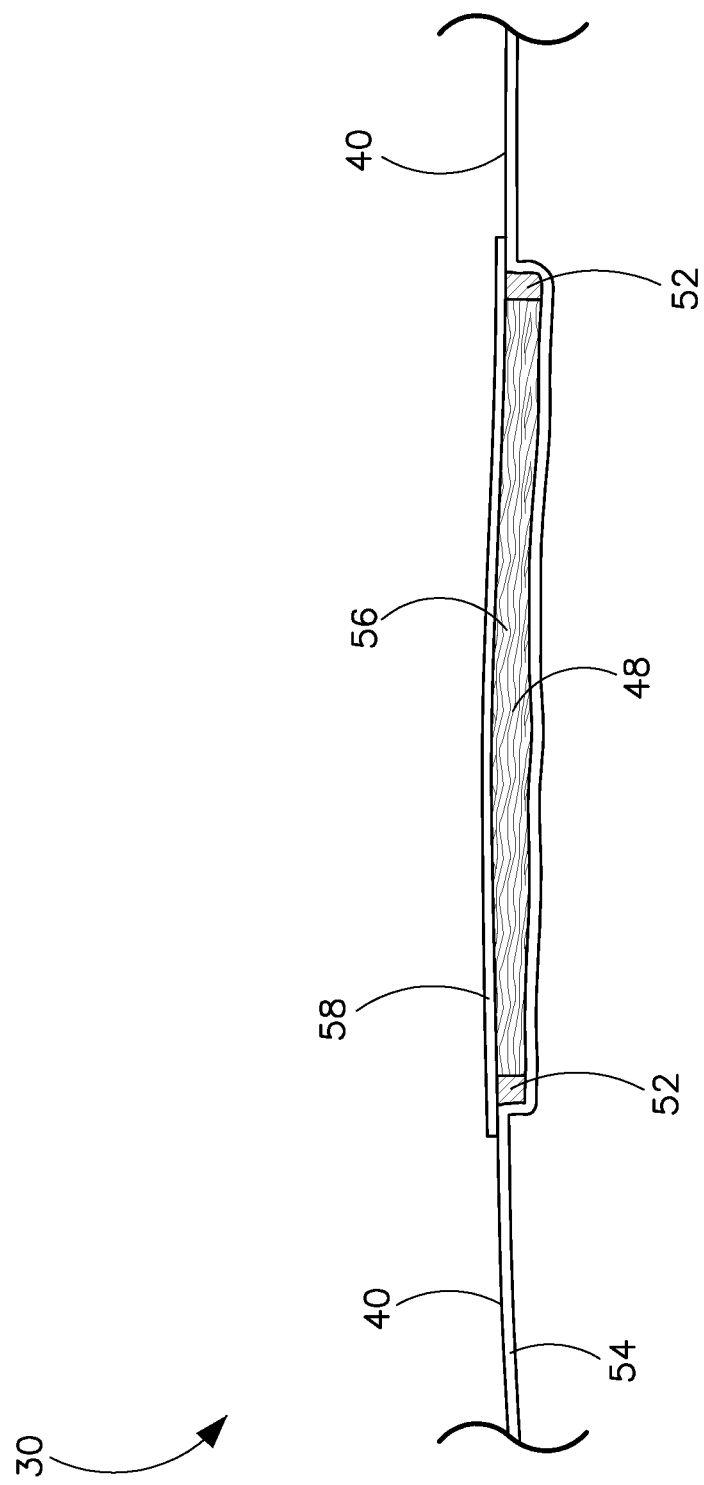
FIG. 5 illustrates a cross sectional side view of the liner of FIG. 1. A plastic removable film is shown in contact with an upper surface of the absorbent material and a perimeter of the liner to keep the absorbent material moist when preloaded with a fluid.

The liner includes an exterior or bottom 54 that can be made from the flexibly deformable material substantially impermeable to fluids, as shown in FIGS. 4-6. The exterior can contact the interior, rim and/or lip of the tray. The exterior or bottom can be configured as a bottom layer of the liner where the flexibly deformable material 40, perimeter 52 and absorbent material are layered on top of the bottom layer.

Figure 8:
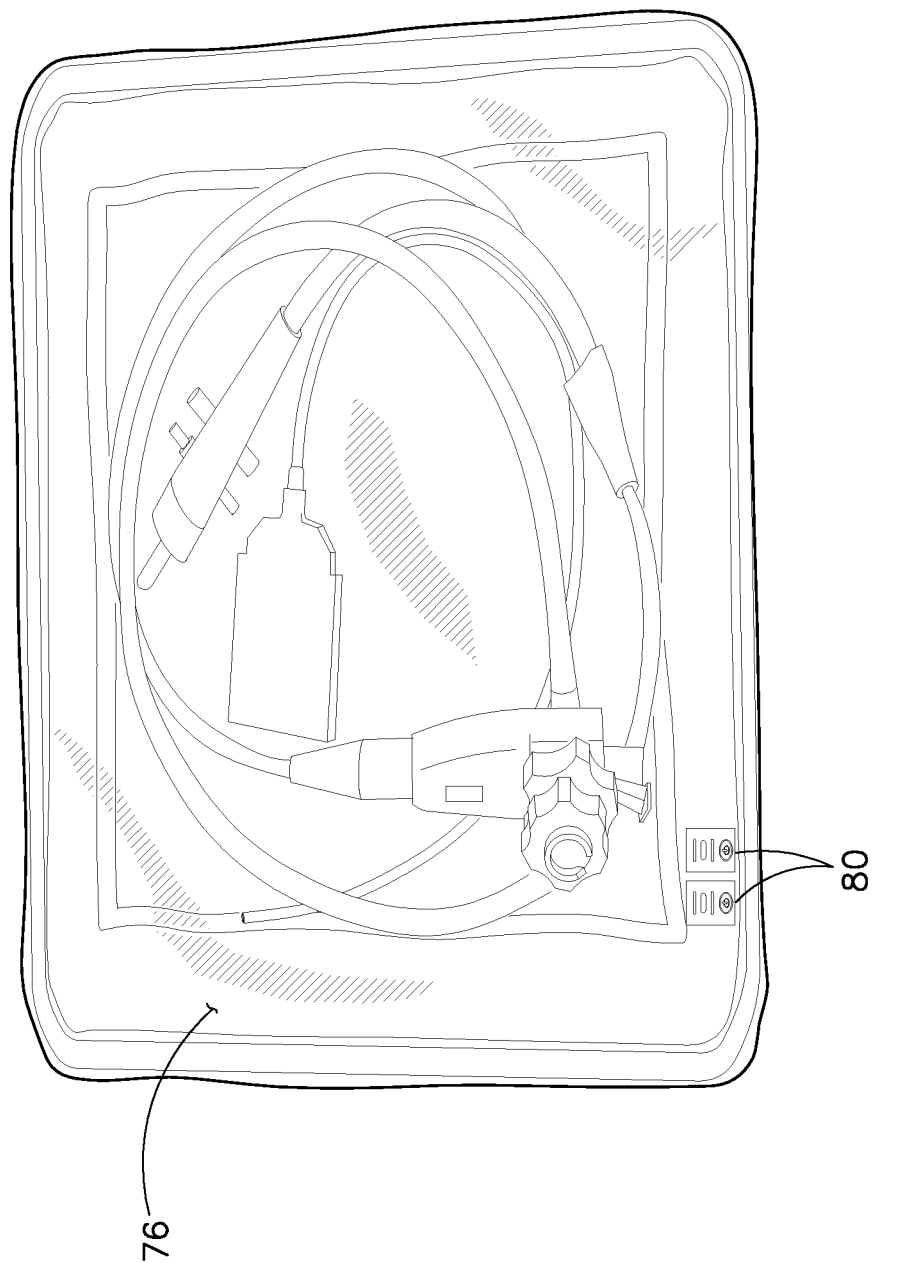
FIG. 8 is a perspective view of a cover temporarily secured to the tray of FIG. 1. A timing mechanism is attached to the cover. In this embodiment, the timing mechanism is a chemically activated timer.

The absorbent material can be contacted with the fluid (e.g., detergent, soap, liquid, etc.) to allow the absorbent material to be saturated with the fluid. In use, the endoscope will contact the absorbent material and the liner will partially enclose the tray and the endoscope as shown in FIG. 1. In this way, the tray is protected from the biofilm or contaminants on the endoscope and the wet absorbent material will provide the moist environment to store the endoscope when the tray is covered as shown in FIG. 8, where the cover also encloses the endoscope. The moist environment will reduce the drying of the biofilm or contaminants on the endoscope and make them easier to remove during reprocessing. In this way, the endoscope can be efficiently cleaned, and a high level of disinfection can be maintained after reprocessing.

The absorbent material can be loaded with a fluid 56 before (pre-loaded) or after the liner is disposed within the tray. For example, as shown in FIG. 5, the absorbent material can be preloaded with the fluid during manufacture and a plastic removable film 58 can engage the absorbent material and the perimeter to maintain moisture within the absorbent material. The plastic film can be a certain thickness and can be made from an impermeable plastic material to prevent the absorbent material from drying. The thickness of the plastic film can be from 1, 2, 3 to about 4 mm.

The plastic film can help the absorbent material stay moist for a period of time, such as, for example, 1 week to about 1 year. The time period can be from about 1, 2, 3, 4, 5, 6, 7, 8, 9, 10, 15, 20, 25, 30, 35, 40, 45, 50 to about 52 weeks (1 year). Additives can be added to the fluid and/or absorbent liner to help maintain moisture within the absorbent material. Additional fluid can be added to the pre-loaded absorbent material if desired.

The absorbent material can be pre-loaded with an amount of the fluid. For example, the amount of fluid that can be pre-loaded into the absorbent liner can be from about 0.1 to about 30 cubic centimeter (cc) in volume of fluid or from about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29 to about 30 cc in volume.

The fluid and the liner can create a moist environment for the endoscope for up to 72 hours or from about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71 to about 72 hours.

In some embodiments, as shown in FIGS. 6A and 6B, the absorbent material can be configured as a separate detachable component so that an existing liner can be converted into an absorbent liner. As shown in FIG. 6A, a second plastic removable film 60 engages with a bottom mating surface 62 of the absorbent material. The mating surface can include an adhesive or other attachment means to facilitate attachment to a corresponding mating surface 63 on an existing liner, as shown in FIG. 6B. The mating surface of the absorbent material allows the absorbent material to be peeled and repositioned (e.g., "peel and stick") at the desired mating surface location on the liner. The second plastic removable film will prevent adhesive on the mating surface of the absorbent material from being used or damaged before it can be utilized for attachment to the existing liner.

The mating surface of the existing liner can include an adhesive or can be configured without an adhesive. Other attachment means can be implemented. In this embodiment, the absorbent material can be manufactured pre-loaded with the fluid or manufactured without the fluid preloaded thereon. In use, a user can remove the second plastic removable film from the bottom mating surface of the absorbent material by peeling it off. The absorbent material can then be attached to the existing liner at the corresponding mating surface.

The mating surfaces can include an adhesive and/or an attachment means such as, for example, clips, snaps, a hook and loop fastener such as Velcro®, magnets, tape, two-sided tape, zippers, button/hole engagements, toggles, hook and eye fasteners, eyelets, grommets, or a combination thereof.

The absorbent material, in some embodiments, can have two opposed surfaces, where one of the opposed surfaces is configured to contact the endoscope as shown in FIG. 1, while the other surface of the absorbent material can contact the liner as shown in FIG. 6B.

The absorbent material, in some embodiments, can have two opposed surfaces, where one of the opposed surfaces is configured to contact the endoscope as shown in FIG. 1, while the other surface of the absorbent material can be covered by a portion of the liner, also shown in FIG. 1. In this way, the absorbent material can have one surface that contacts the endoscope, while the other surface contacts the liner or the bottom interior of the tray.

It will be understood by those of ordinary skill in the art that the absorbent material can have a surface area that is smaller than the liner. In some embodiments, the absorbent material can have a surface area that is larger, the same size or smaller than the surface area of a coiled flexible endoscope.

The liner can be configured in various colors. For example, the liner can be white, clear, blue, yellow and/or red. The liner can also be transparent, semi-transparent and/or opaque. The flexibly deformable material can be the same or different color than the absorbent material.

The liner can be a certain size and/or shape. For example, the liner can be from about 24 inches to about 40 inches, having a width from about 20 inches to about 30 inches. The shape of the liner can be rectangular, but other shapes are contemplated. The liner can also be in a sheet configuration. Various portions of the liner can also be manually cut by a user to tailor the liner to a particular tray size.

In some embodiments, contaminants can include, but are not limited to, biological contaminants such as bodily fluids, fecal matter, microorganisms including bacteria, viruses, yeasts, molds and parasites; airborne contaminants such as airborne microbes; and/or chemical contaminants. In some embodiments, bacteria can include, but is not limited to *Escherichia coli, Klebsiella* species, *Enterobacter* species, enterococci, *Pseudomonas aeruginosa* and *Salmonella* species.

Storage System

Referring to FIGS. 1-20, an endoscope storage system 64 is provided. The system includes the tray 32. The tray can be rigid and/or reusable. In some embodiments, the tray is similar to the tray described in U.S. Pat. No. 6,749,063, assigned to Cantel (UK) Limited. This patent is herein incorporated by reference.

Figure 9:
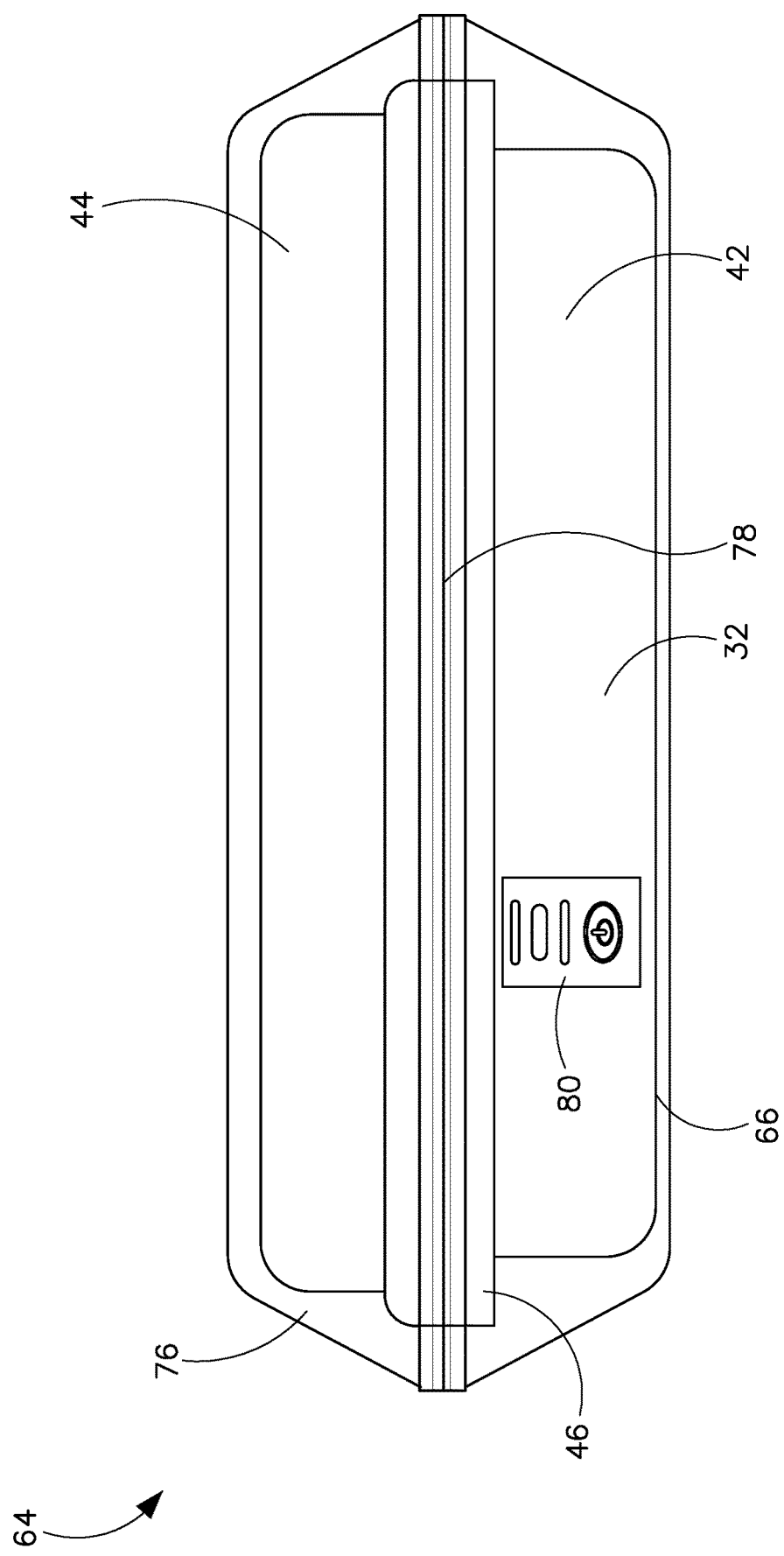
FIG. 9 illustrates a side view of the tray of FIG. 1 disposed within a bag configuration of the cover of FIG. 8. A timing mechanism is attached to the tray.

As described above, the tray includes the interior 34, surrounding sidewalls 42, rim 44 that curls over to form the peripheral lip 46. The peripheral lip is disposed at least partially around the surrounding sidewalls and extends outwardly therefrom. A base or bottom surface 66 of the tray contacts the surrounding sidewalls, as shown in FIG. 9. The surrounding sidewalls can be continuous and monolithic with the base or bottom surface of the tray. As shown in FIGS. 1, 3, 14, 16 and 17-19, the interior of the tray can be planar.

Figure 7:
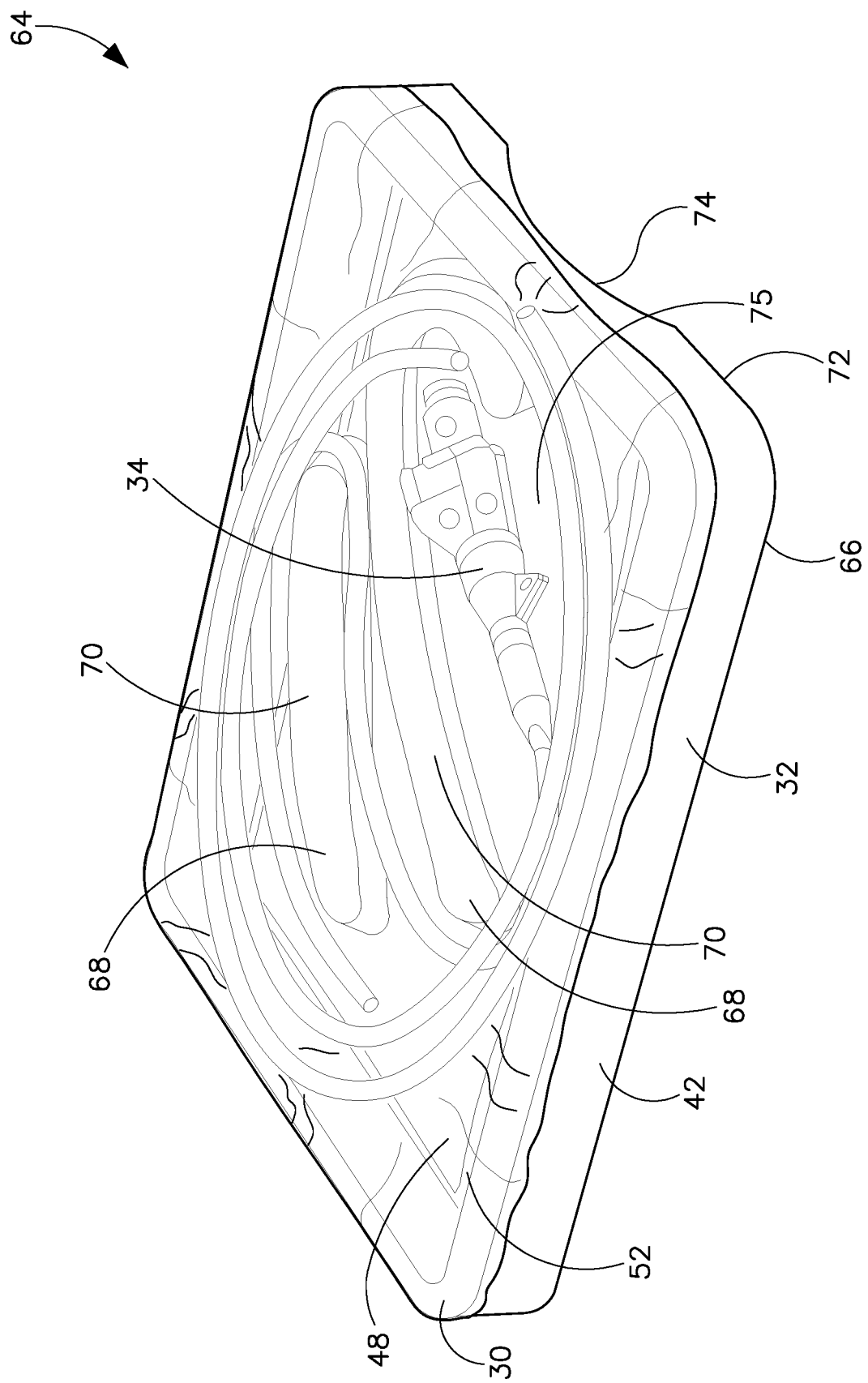
FIG. 7 illustrates a perspective view of an embodiment of the tray of FIG. 1. The interior of the tray comprises at least two upstanding elements spaced apart from each other to provide support for a flexible medical endoscope coiled between all or a portion of the at least two upstanding elements. The liner is shown covering the interior of the tray.

Alternatively, as shown in FIG. 7, the interior of the tray can define at least two upstanding elements 68 spaced apart from each other configured to provide support for the flexible medical endoscope 34 coiled between all or a portion of the at least two upstanding elements. The absorbent material of the liner can engage the interior of the tray adjacent to the at least two upstanding elements. A top surface 70 of the at least two upstanding elements aligns with the rim of the tray on a same plane, as shown in FIG. 7.

The base or bottom surface of the tray can have planar 72 and/or non-planar 74 portions and the surrounding sidewalls upstand therefrom. The interior of the tray can also have planar surfaces 75. The tray can be formed of a semi-rigid material capable of withstanding repeated disinfection and dimensioned to provide support for the flexible medical endoscope coiled in a stress-free state.

The absorbent material, in some embodiments, can contact the stored endoscope and also be positioned adjacent to the upstanding elements and contour the upstanding elements so that moisture can be provided to the endoscope and the environment surrounding the endoscope to reduce or prevent the biofilm and/or contaminants from drying on or in the channels of the endoscope.

The absorbent material, in some embodiments, can be placed adjacent to the planar surfaces of the interior of the tray adjacent to the upstanding elements so that the absorbent material can contour the upstanding elements so that moisture can be provided to the endoscope and the environment surrounding the endoscope to reduce or prevent the biofilm and/or contaminants from drying on or in the channels of the endoscope.

The system can include a cover 76, as shown in FIGS. 8, 9, 13, 17 and 18. The cover can be a disposable single use cover that may be sterile or unsterile configured to engage at least the rim of the tray. In some embodiments, the cover has some similar features to the cover found and described in U.S. Pat. No. 6,749,063, assigned to Cantel (UK) Limited. This patent is herein incorporated by reference.

The cover comprises a flexibly deformable material 76 that is substantially impermeable to fluids so as to protect the endoscope from external fluids that can contaminate the endoscope. The flexibly deformable material is configured to be temporarily secured to the tray so as to cover at least the interior of the tray.

The cover can be in a sheet, wrap or bag configuration, as shown in FIGS. 8, 9, 13, 17 and 18. The sheet, wrap or bag configuration can have a rectangular shape to correspond with the shape of the tray but other cover shapes are contemplated depending on tray shape. These shapes include oval, square, circular or the like.

The flexibly deformable material of the cover can be configured to entirely enclose/extend over the tray, such as when the cover is in the bag configuration, as shown in FIG. 9. The cover can be a sealable bag. The flexibly deformable material can include a zip seal 78 or adhesive seal to enclose the tray. Alternatively, the flexibly deformable material can be configured to partially enclose the tray, such as when the cover is in a sheet or wrap configuration, as shown in FIGS. 8, 13, 17 and 18.

The cover can be manufactured in different colors, such as in a red color, to indicate that the endoscope is contaminated and needs to be reprocessed, or a green color to indicate that the endoscope is clean and ready for use. Alternative colors can be selected, such as blue, pink, yellow, red, orange, brown or black. In some embodiments, the cover can be reversible and a different color can be used on the inner surface than on the outer surface of the cover.

The cover can be manufactured at a certain sheet thickness. In some embodiments, the sheet thickness of the cover can be from about 100 micrometers ($\mu$m) to about 4 millimeters (mm). In some embodiments, the sheet thickness of the cover can be from about 100 $\mu$m, 200 $\mu$m, 300 $\mu$m, 400 $\mu$m, 500 $\mu$m, 600 $\mu$m, 700 $\mu$m, 800 $\mu$m, 900 $\mu$m, 1 mm, 2 mm, 3 mm to about 4 mm.

The cover can have certain dimensions such as, from about 18 inches to about 30 inches in length and from about 14 to about 24 inches in width. In some embodiments, the dimensions of the cover are from about 18, 19, 20, 21, 22, 23, 24, 25, 26, 27, 28, 29 to about 30 inches in length and from about 14, 15, 16, 17, 18, 19, 20, 21, 22, 23 to about 24 inches in width.

The flexibly deformable sheet material of the cover can be made from a high-density polythene (HDP). In some embodiments, the flexibly deformable sheet material can be made from other materials such as, for example, high-density polyethylene (HDPE), low-density polyethylene (LDPE), and/or linear low-density polyethylene (LLDPE).

As shown in FIGS. 8-13, and 16 the system can include a timing mechanism 80 that can engage with a surface of the liner, the cover and/or the tray. The timing strip will indicate to a user the amount of time that has elapsed since the end of a procedure and when the contaminated endoscope was first disposed in the tray. The timing mechanism can be a chemical or digital timing strip. The user sets the amount of time and/or date to determine how long the endoscope was stored in the tray before reprocessing.

FIGS. 8-11 and 16 show the timing mechanism as a chemical strip that can be manually activated by a user. As shown in FIG. 10, the chemical strip can have an activation button 82 that is manually pressed by a user to activate the strip. The strip includes a first outer layer 84, a second intermediate layer 86 and a third backing layer or bottom 88.

The first outer layer includes the activation button, a time increment marker 90 and viewing windows 92 to visually indicate to a user the period of time since activation of the chemical strip has occurred. The second intermediate layer can be made from a porous membrane material for which a chemical and/or fluid located inside of the strip travels through. Pressing the activation button releases the chemical and/or the liquid from a blister 94. A colored line 96 will appear after the activation button is pressed to confirm that the chemical strip is active. As time passes, the colored line will progress and when the viewing windows are completely filled, the full time period has elapsed.

In some embodiments, a suitable chemical strip that can be used in the current application to monitor time is available from Timestrip UK Ltd, of Sheraton House, Castle Park, Cambridge CB3 0AX United Kingdom as Timestrip® 1 hour or Timestrip® 12 hours.

In some embodiments, the chemical strip is attached to a surface of the liner, cover and/or tray by an adhesive 98 that is attached to the back of the third backing layer or bottom. In some embodiments, the adhesive can be a pressure sensitive adhesive and/or a removable adhesive. In some embodiments, the adhesive can be manufactured from a glue, rubber, acrylic, and/or an epoxy.

Figure 13:
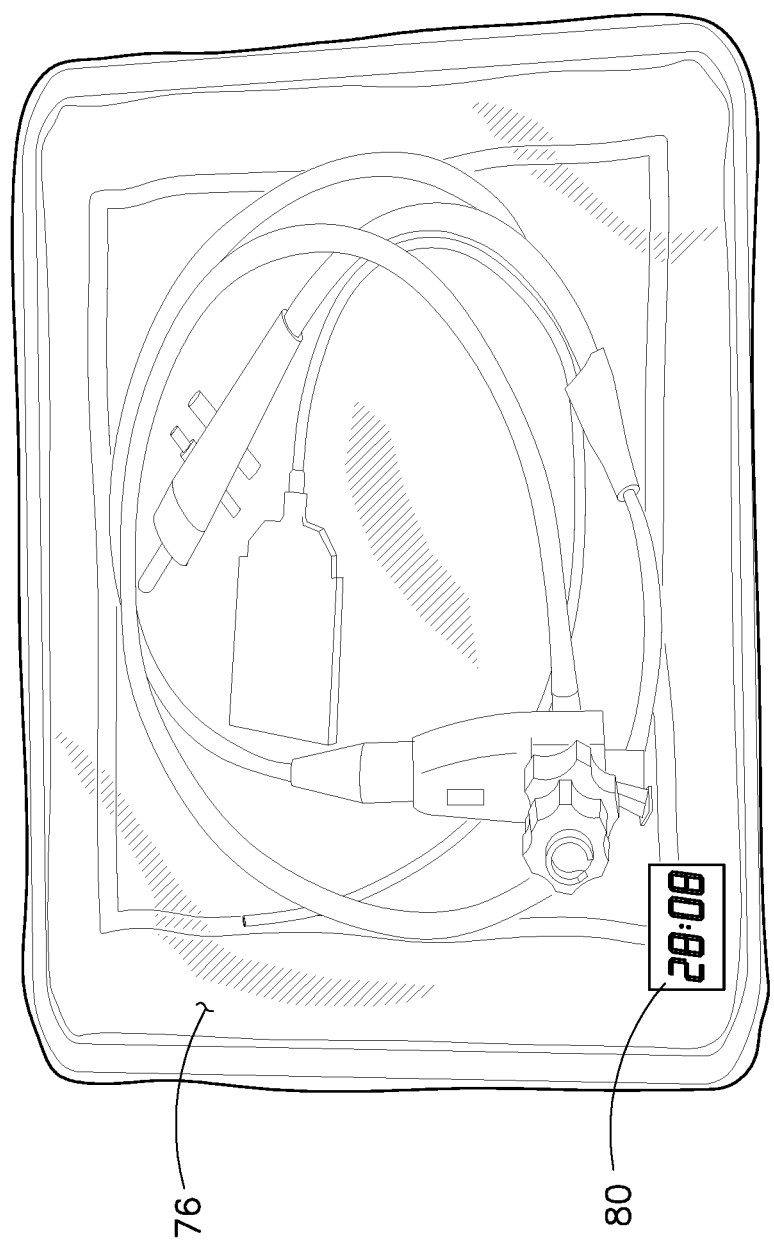
FIG. 13 illustrates a perspective view of the cover and tray of FIG. 8. In this embodiment, the timing mechanism is digital.

As shown in FIGS. 12 and 13, the timing mechanism can also be a digital timing strip. The digital timer can be attached to a surface of the liner, cover and/or tray in the same manner as the chemical strip described above. The digital timing strip can be removable and can be rechargeable.

Figure 14:
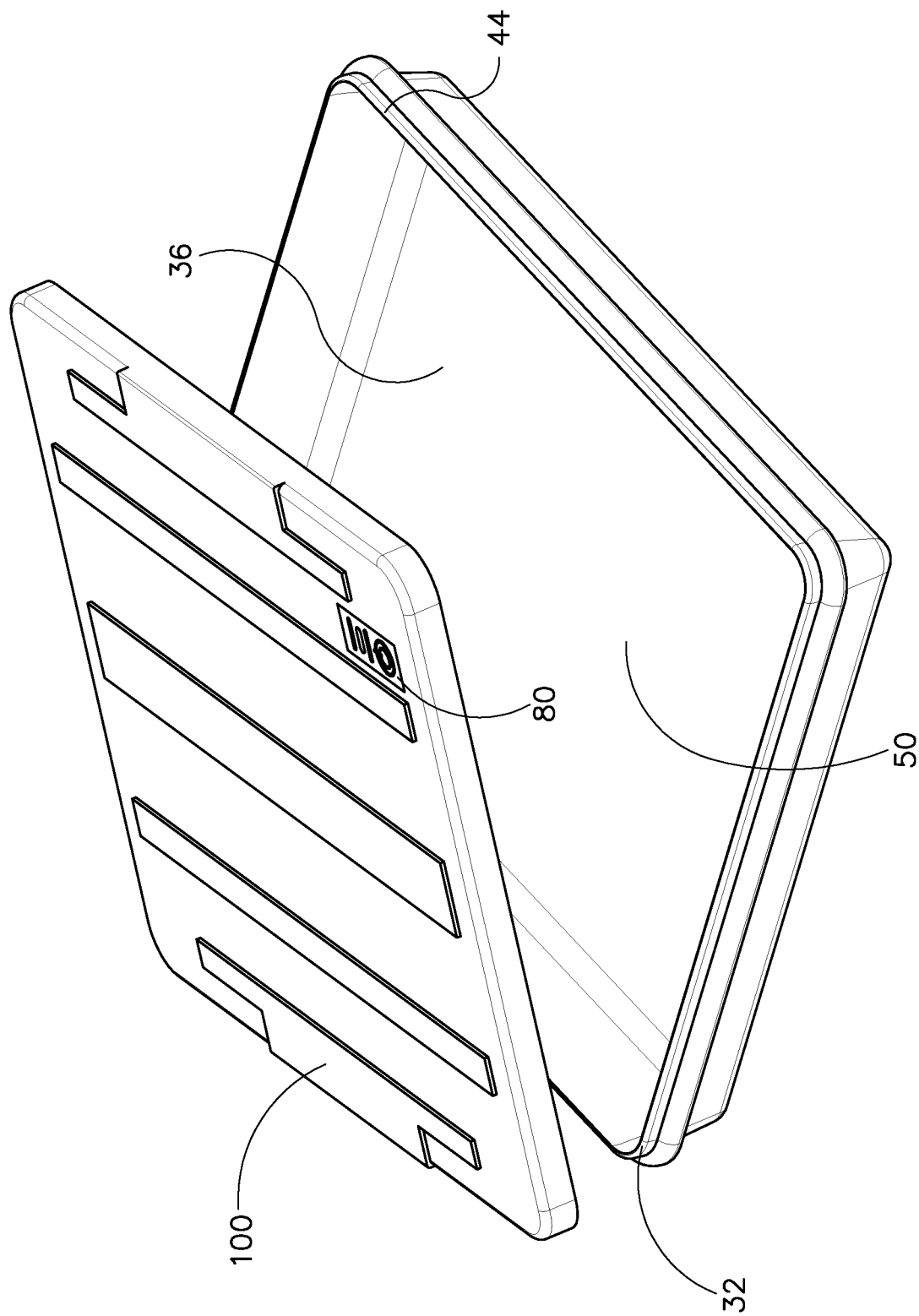
FIG. 14 illustrates a perspective view of the tray of FIG. 1 and a rigid lid that engages with a portion of the tray to close the tray.
Figure 15:
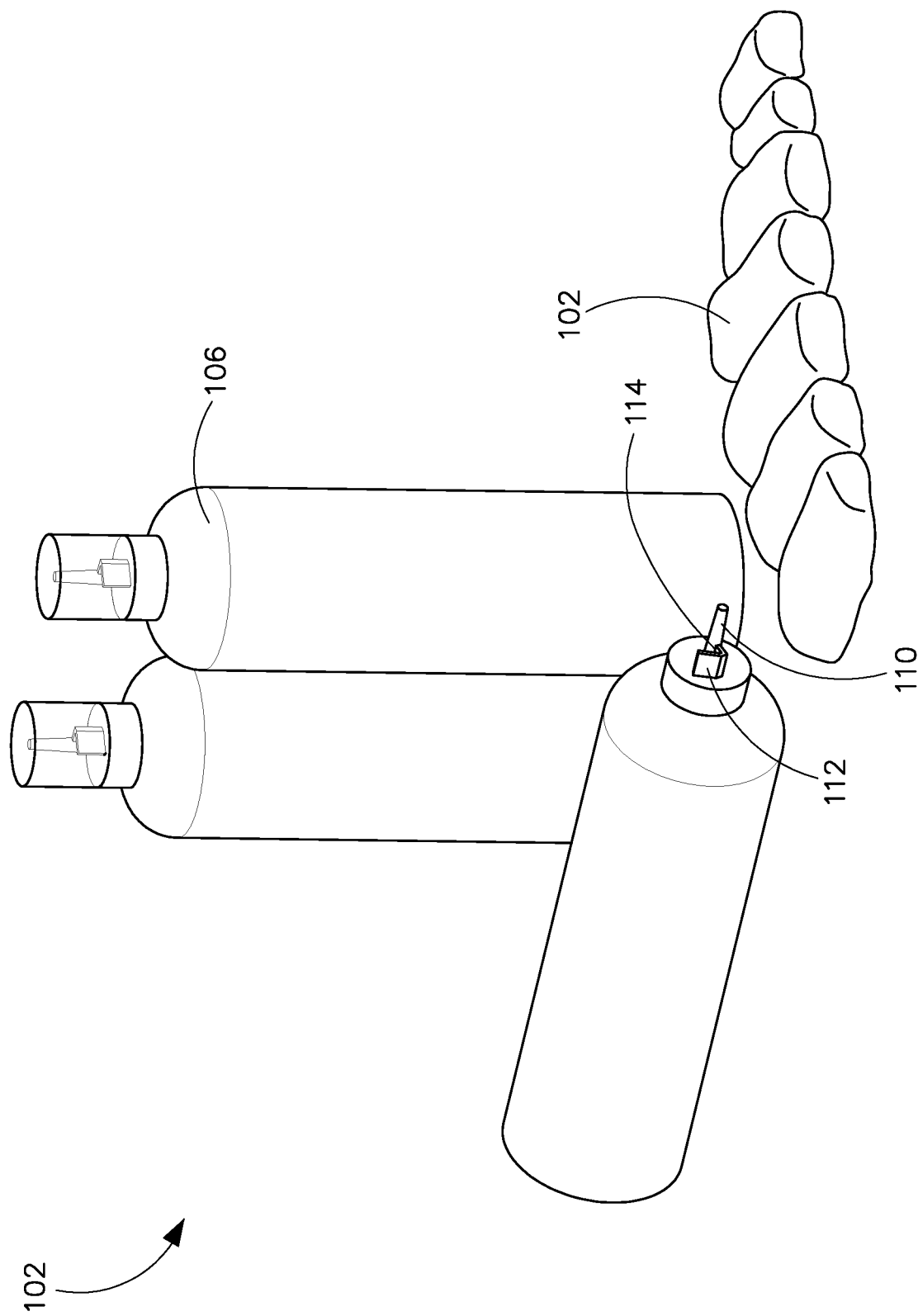
FIG. 15 illustrates a perspective view of detergent containers. The detergent is dispensed manually or automatically on an exterior surface of the endoscope and/or interior surfaces of the endoscope to keep the endoscope moist while the endoscope waits to be reprocessed.

The system can include a rigid lid 100 shown in FIG. 14 that is configured to engage with the rim of the tray to seal the tray closed. The timing mechanism can also be coupled to the rigid lid and tray. This timer can indicate to the user the amount of time that the endoscope was stored before or after reprocessing.

The system can include fluid 56 which can be in the form of a detergent 102, as shown in FIGS. 15, 16 17 and 18. An amount of the detergent is configured to be dispensed manually or automatically to an exterior surface of the endoscope and/or interior surfaces or channels 104 of the endoscope to keep the endoscope moist and/or clean prior to reprocessing. The detergent coupled with the liner provides a moist environment for the contaminated endoscope. The detergent can be a foam detergent, for example, Intercept™ Foam, owned by Medivators Inc. located in Minneapolis, MN, U.S.A. The foam can be a pressurized foam that is stored in a detergent container 106.

The foam detergent can be a pre-conditioning detergent that maintains a moist environment for the endo scope to prevent contaminants and/or organic debris from drying and hardening on or within the endoscope. The foam detergent can be configured to immediately loosen contaminants and/or gross bioburden from an exterior surface 108 of the endoscope prior to manual/automatic cleaning of the endoscope. The foam detergent or pressurized foam detergent can also be configured to preclean the endoscope stored within the interior of the tray.

Figure 16:
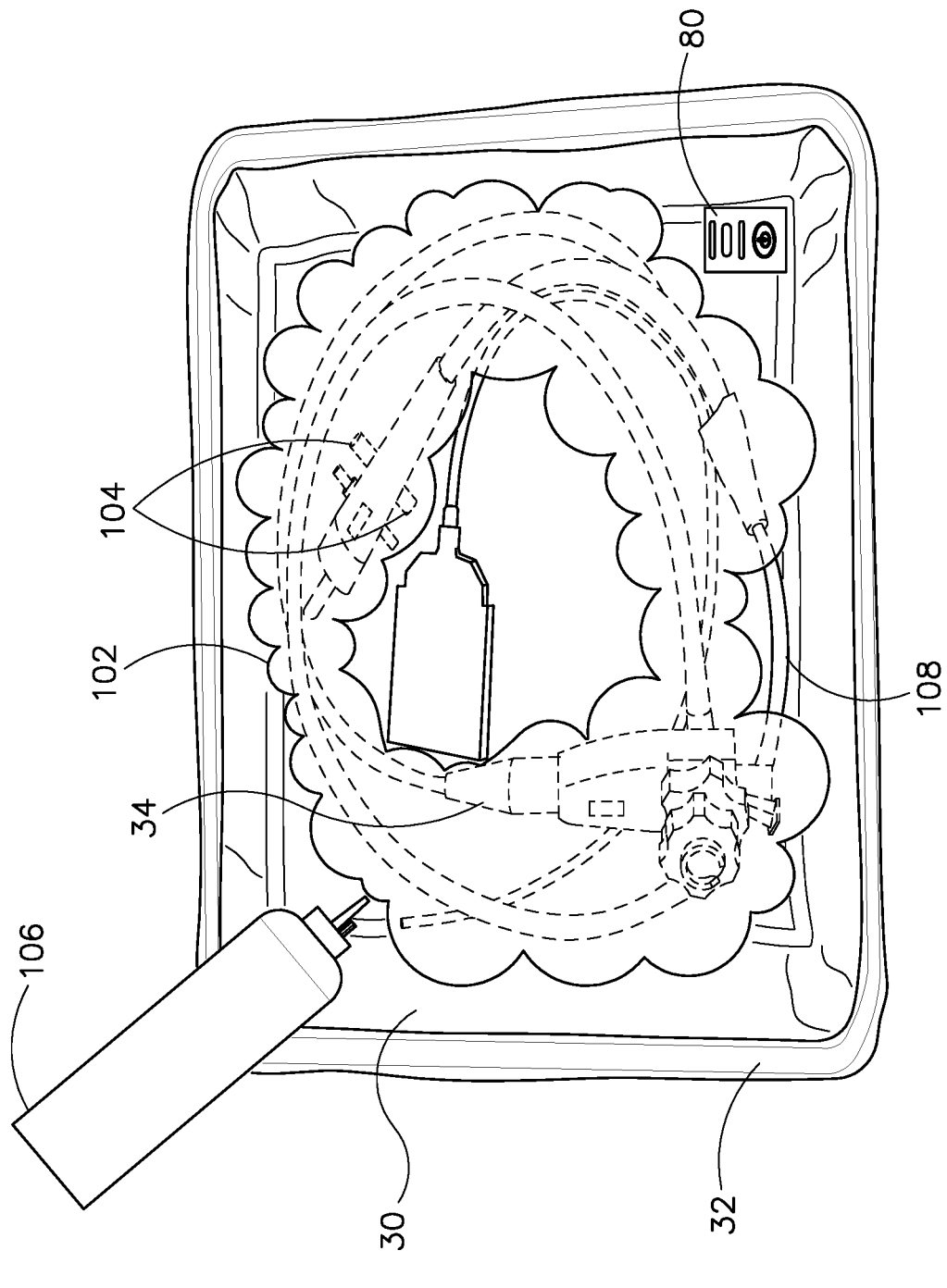
FIG. 16 illustrates a perspective view of the liner, tray and endoscope of FIG. 1. In this embodiment, the detergent is manually dispensed on the exterior surface and interior surfaces of the endoscope. A timing mechanism is also shown attached to the liner.

The detergent container includes an outlet 110 and a surface 112 adjacent to the detergent container having an actuation button 114 configured to control dispensing of the detergent from the detergent container. When the detergent is dispensed manually, a user will activate the detergent container to dispense the detergent by applying force in a direction on the actuation button of the detergent container, as shown in FIG. 16.

Figure 17:
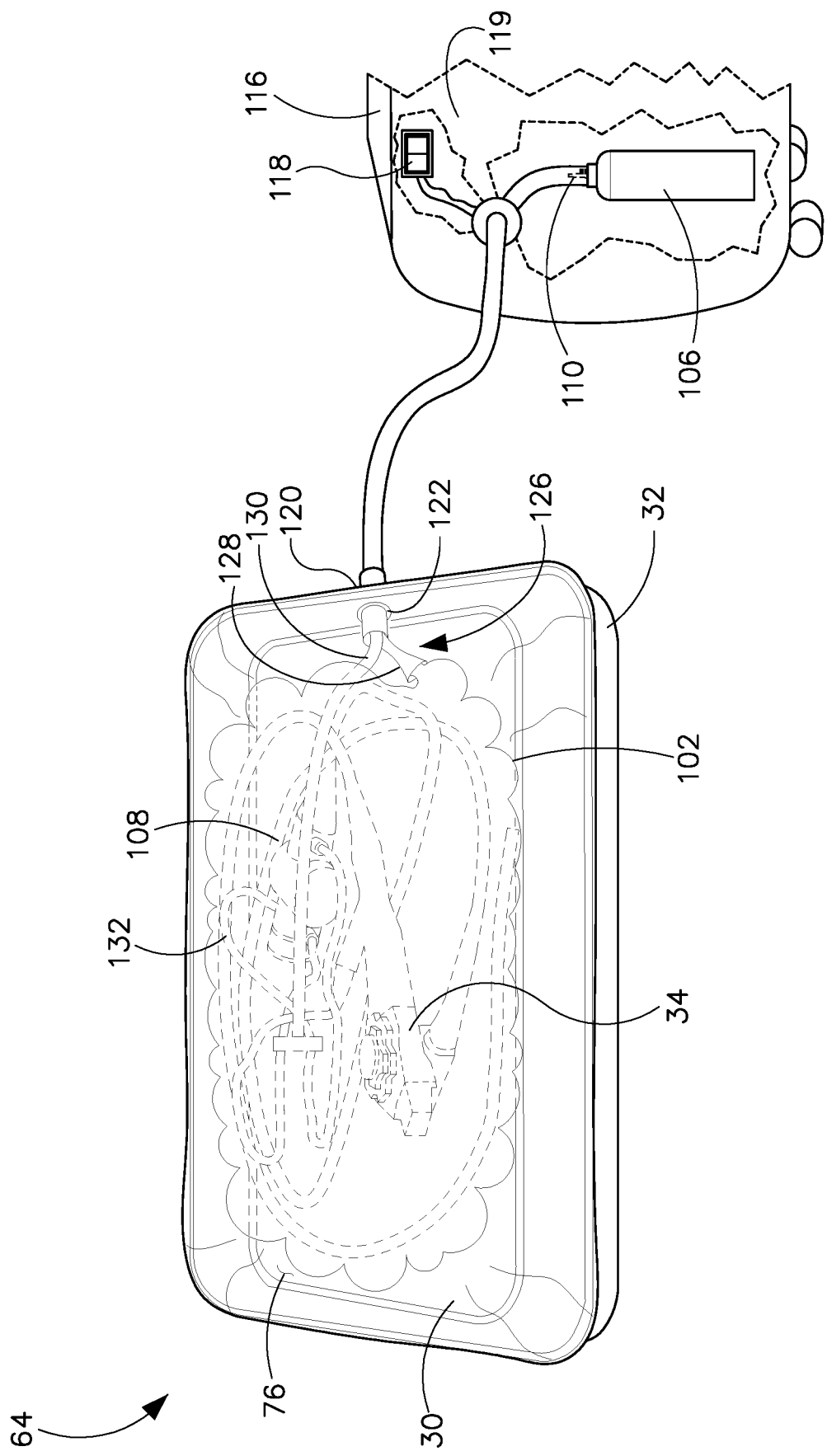
FIG. 17 illustrates a perspective view of an endoscope storage system. The system comprises the cover and liner of FIG. 1. The system further includes a detergent container having an outlet configured to dispense detergent to an inlet of the cover, liner and/or endoscope storage tray and to the interior of the endoscope storage tray. In this embodiment, the tray includes the inlet. A machine is shown dispensing the detergent.
Figure 18:
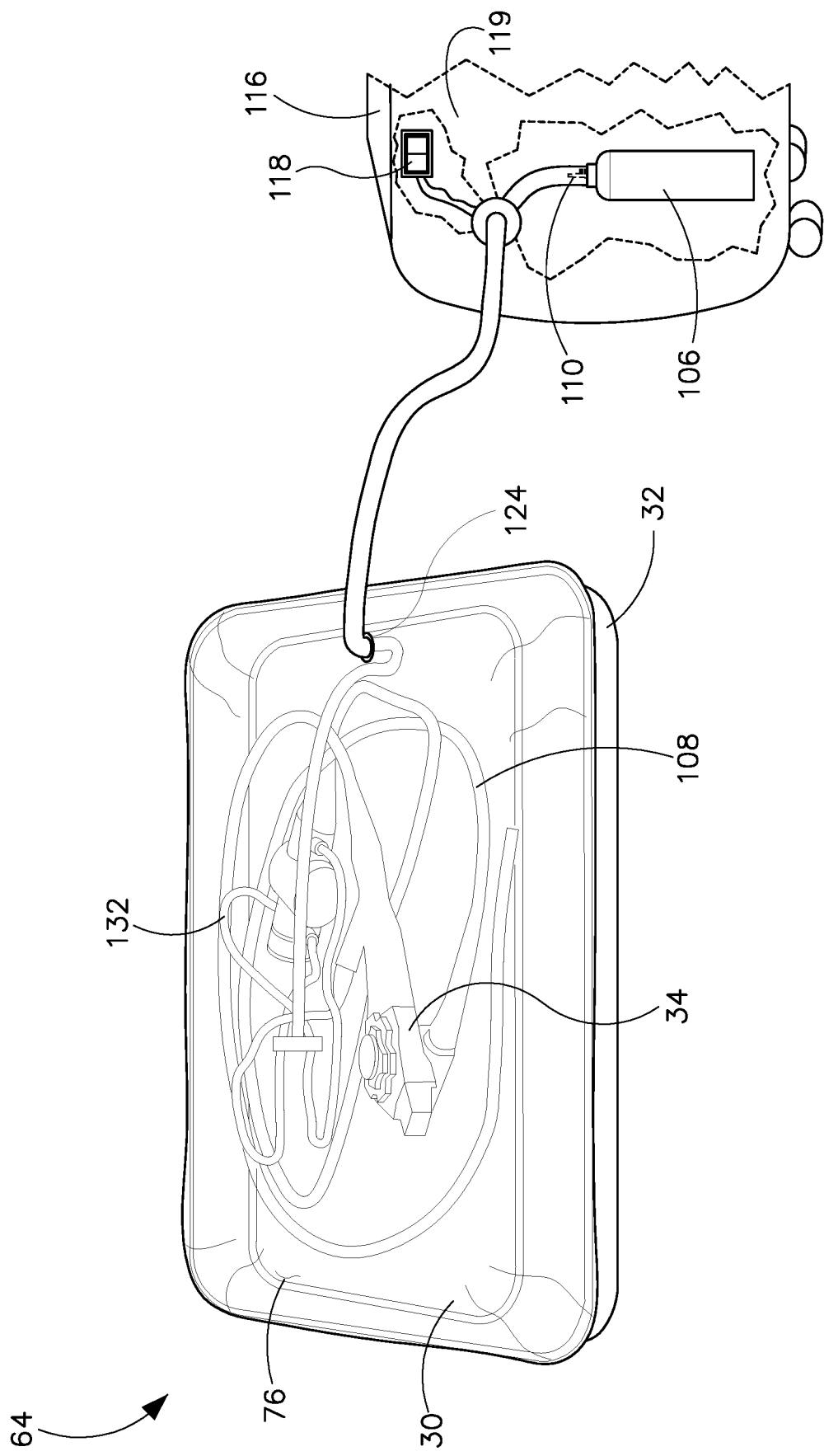
FIG. 18 illustrates a perspective view of an endoscope storage system. The system comprises the cover and liner of FIG. 1. The system further includes a detergent container having an outlet configured to dispense detergent to an inlet of the cover, liner and/or endoscope storage tray and to the interior of the endoscope storage tray. In this embodiment, the cover includes the inlet. A machine is shown dispensing the detergent.
Figure 19:
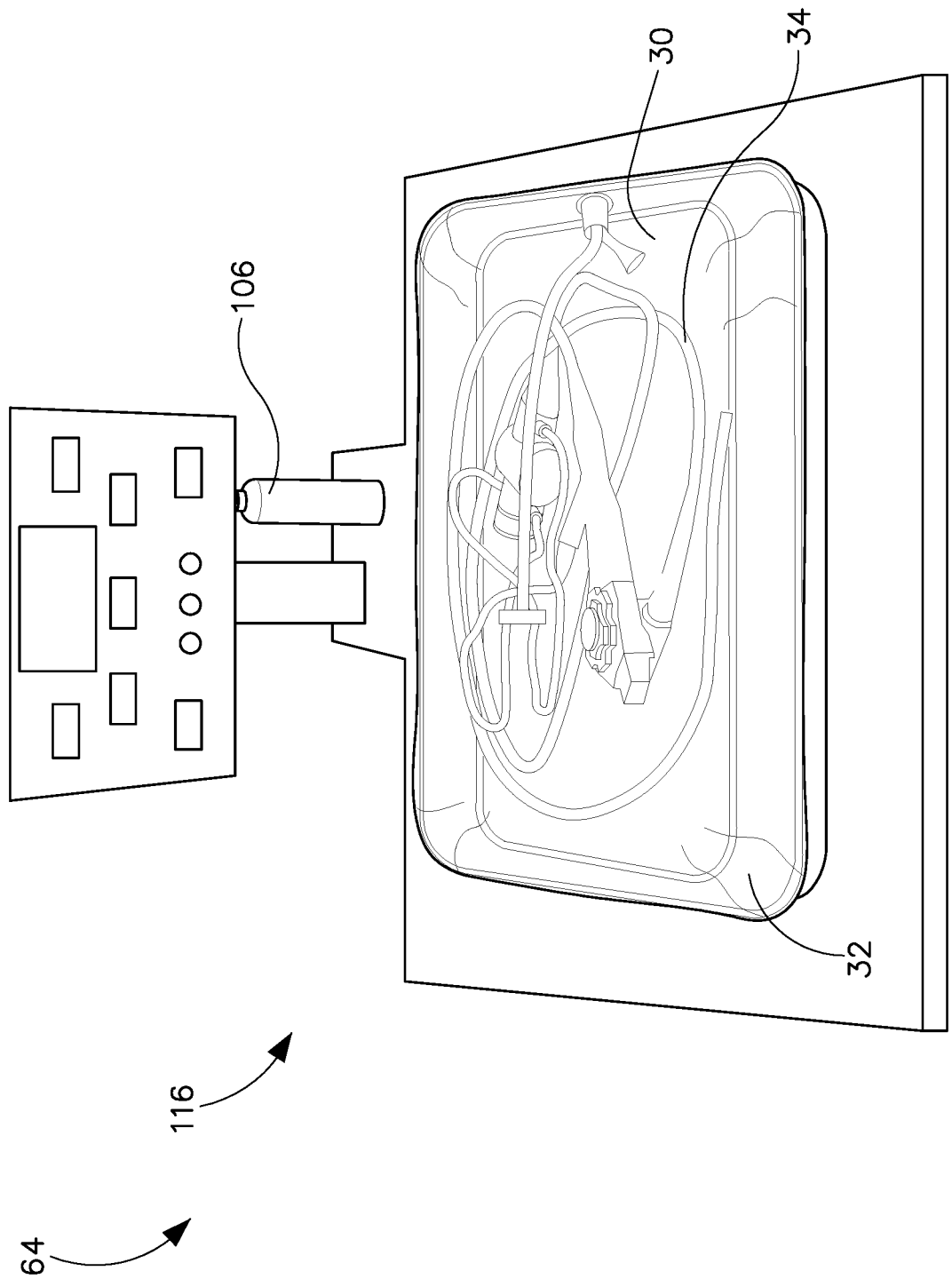
FIG. 19 illustrates a perspective view of an endoscope storage system similar to FIG. 17.

The detergent can be dispensed automatically within or on the endoscope, as shown in FIGS. 17-19. When the detergent is dispensed automatically, the detergent container can be dispensed through an automated machine 116. As shown in FIGS. 17-18, the detergent container can be inserted into the machine and is activated/controlled by an on/off actuation button 118 on the machine that is disposed on a surface 119 that is adjacent to the container and/or an inlet, as described below. The foam detergent is dispensed through the outlet and through an inlet in the tray 120 and/or an inlet in the liner 122 (FIG. 17) or through an inlet in the cover 124 (FIG. 18), and into the interior of the tray. The inlet of the tray, liner and/or the cover can engage one or more channels of the endoscope.

The inlet comprises a connector 126, as shown in FIG. 17, that includes a first port 128 and a second port 130. The first port is configured to dispense the detergent to the exterior of the endoscope and the second port is connected to a channel or channels of the endoscope and is configured to dispense detergent into the channel or channels of the endoscope. Tubing 132 can be connected to the second port to assist in dispensing the detergent to the channels of the endoscope, as shown in FIG. 17.

As shown in FIG. 19, the automated machine can also be similar to the preconditioning apparatus described in PCT/US2018/018489, assigned to Medivators Inc. This application is herein incorporated by reference.

The foam detergent can encapsulate the exterior surface of the endoscope, as shown in FIGS. 16-18 for up to 72 hours or from about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71 to about 72 hours. The foam detergent can also be easily rinsed off of the endoscope when it is time to reprocess the endoscope.

The amount of foam detergent applied within or on the endoscope can be from about 0.1 cc, 0.2 cc, 0.3 cc, 0.4 cc, 0.5 cc, 0.6 cc, 0.7 cc, 0.8 cc, 0.9 cc, 1 cc, 2 cc, 3 cc, 4 cc, 5 cc, 6 cc, 7 cc, 8 cc, 9 cc, 10 cc, 11 cc, 12 cc, 13 cc, 14 cc, 15 cc, 16 cc, 17 cc, 18 cc, 19 cc, 20 cc, 21 cc, 22 cc, 23 cc, 24 cc, 25 cc, 26 cc, 27 cc, 28 cc, 29 cc, 1 ounce, 2 ounces, 3 ounces, 4 ounces, 5 ounces, 6 ounces, 7 ounces, 8 ounces, 9 ounces, 10 ounces, 11 ounces, 12 ounces, 13 ounces, 14 ounces, 15 ounces, 16 ounces, 17 ounces, 18 ounces, 19 ounces, 20 ounces, 21 ounces, 22 ounces, 23 ounces, 24 ounces, 25 ounces, 26 ounces, 27 ounces, 28 ounces, 29 ounces, 30 ounces, 31 ounces to about 32 ounces of the foam detergent.

As described above, when the foam detergent is Intercept™ Foam, 1 to about 10 or 1, 2, 3, 4, 5, 6, 7, 8, 9 to about 10 Intercept™ Foam containers can be applied within or on the endoscope.

Figure 20:
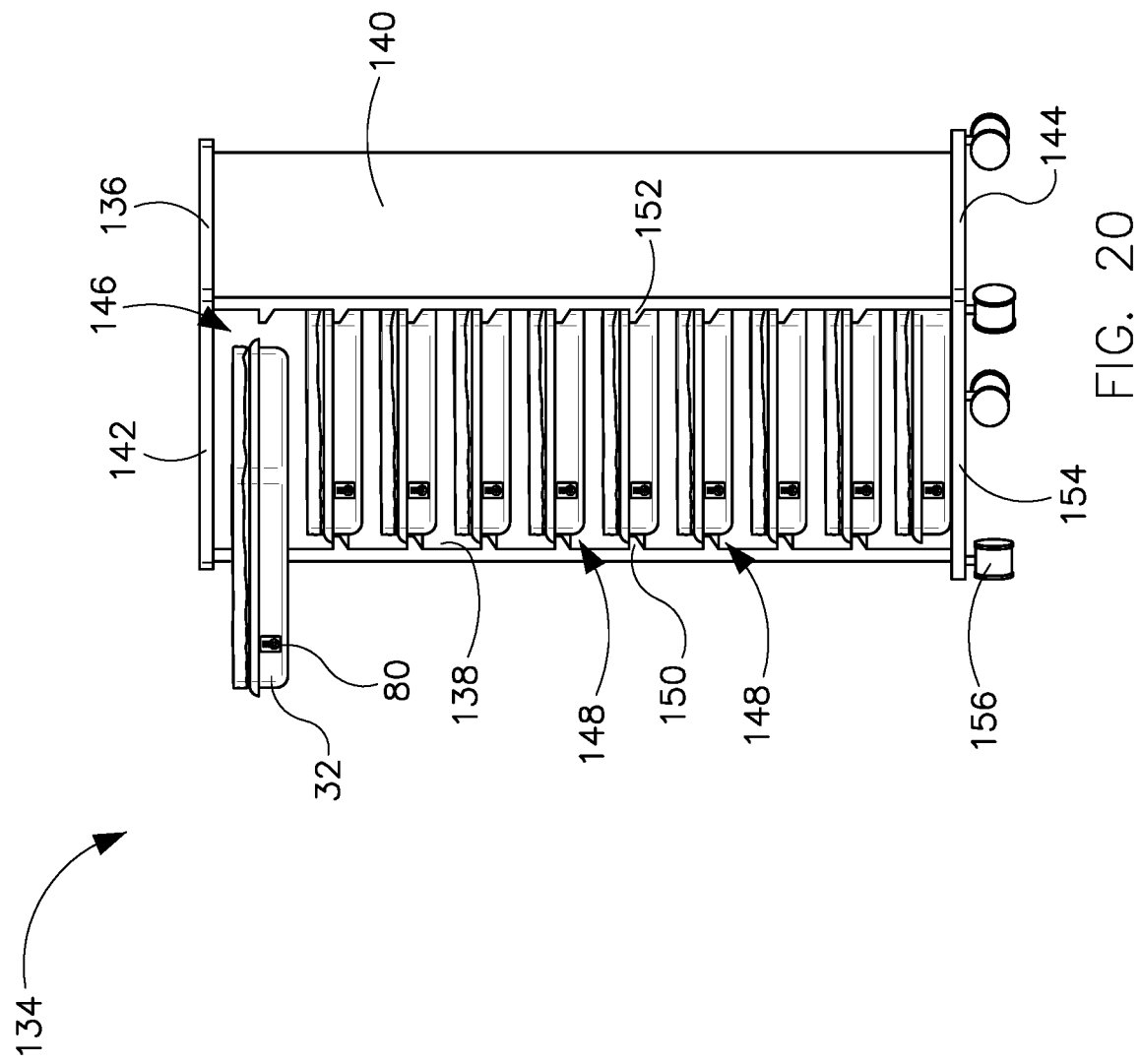
FIG. 20 illustrates a perspective view of a cart that is included in the system of FIGS. 17 and/or 18. The cart is configured for storing the tray.

As shown in FIG. 20, the system can include a cart 134 configured to store and/or transport one or more trays. The trays can be stored in the cart in a stacked configuration. The cart comprises a housing 136. The housing includes opposing side walls 138, 140 and top and bottom walls 142, 144. An interior 146 of the housing comprises one or a plurality of slots 148, each configured to slidably receive the tray. The slots are transverse relative to the opposing side walls. Each slot is defined by ledges 150, 152 that are in parallel orientation relative to each other. The cart can comprise one or more slots, such as 1 to about 12 slots.

The bottom wall includes an exterior surface 154 that attaches to a plurality of wheels 156, such as caster wheels.

The cart can include 4 or more wheels disposed at corners of the exterior surface. The cart can be washed and can be heat and chemical resistant.

In some embodiments, various components of the system can be made from a material such as, for example, a polymeric material. The polymeric material can be thermoplastic and/or is a polycarbonate. For example, components of the system can be fabricated from materials such as machined or injection molded thermoplastics such as polyaryletherketone (PAEK) including polyetheretherketone (PEEK), polyetherketoneketone (PEKK) and polyetherketone (PEK), carbon-PEEK composites, PEEK-BaS04 polymeric rubbers, polyethylene terephthalate (PET), fabric, silicone, polyurethane, silicone-polyurethane copolymers, polymeric rubbers, polyolefin rubbers, semi-rigid and rigid materials, elastomers, rubbers, thermoplastic elastomers, thermoset elastomers, elastomeric composites, polyphenylene, polychloropene, polyamide, polyetherimide, polyethylene, epoxy, partially resorbable materials, totally resorbable materials, polyglycolide, polytyrosine carbonate, polycaprolactone, silicone based rubber, liquid silicone rubber, High Consistency Rubber, silicon, TPE, Polypropylene, Polycarbonate, ABS or any combination thereof.

The components of the system, individually or collectively, may also be fabricated from a heterogeneous material such as a combination of two or more of the above-described materials. The components of the system as described herein may be constructed of a suitable biocompatible material to impart various desirable characteristics, such as flexibility, and resilience.

In some embodiments, components of the system can also be made from a suitable material, such as, for example, polyurethane, polyurea, polyether(amide), PEBA, thermoplastic elastomeric olefin, copolyester, styrenic thermoplastic elastomer, carbon fiber, glass fiber, ceramics, methacrylates, poly (N-isopropylacrylamide), PEO-PPO-PEO (pluronics), plastic (e.g., polycarbonates), ABS, MABS, or the like, or combinations thereof.

In some embodiments, various components of the system may be formed from a suitable material, such as metal, polyurethane, polyurea, polyether(amide), PEBA, thermoplastic elastomeric olefin, copolyester, and styrenic thermoplastic elastomer, carbon fiber, glass fiber, ceramics, methacrylates, poly (N-isopropylacrylamide), rubber, plastic, or the like, or combinations thereof, or any of the materials as described herein.

Methods and Kits

A method of preventing or reducing contaminants from drying in or on an endoscope is provided. The method comprises disposing the endoscope on a liner, the liner having an interior comprising a flexibly deformable material substantially impermeable to fluids and an absorbent material disposed within or attached to at least a portion of the flexibly deformable material of the liner; and applying a fluid to an exterior surface of the endoscope and interior surfaces of the endoscope and/or the absorbent material of the liner. It is to be understood that the liner is liner 20, as described above.

In some embodiments, the fluid is a foam detergent and the exterior surface of the endoscope is encapsulated with the foam detergent for up to 72 hours. In some embodiments, the fluid comprises a detergent, sterile water, tap water or a combination thereof. In some embodiments, the liner is disposable and is sterile or non-sterile.

It will be recognized by one of ordinary skill in the art that numerous steps in the manufacturing process may be optional or may be performed in a different sequence than specifically shown. The scope of the manufacturing process is not limited to the particular sequence and steps discussed herein, except as expressly recited in the claims.

In some embodiments, components of the system described above may be made by injection molding, compression molding, blow molding, thermoforming, die pressing, slip casting, electrochemical machining, laser cutting, water-jet machining, electrophoretic deposition, powder injection molding, sand casting, shell mold casting, plaster-mold casting, investment casting, vacuum casting, permanent-mold casting, slush casting, pressure casting, die casting, centrifugal casting, squeeze casting, rolling, forging, swaging, extrusion, shearing, spinning, or combinations thereof.

In some embodiments, the components of the system may be formed by 3D printing. The terms "three-dimensional printing system," "three-dimensional printer," and "printing," describe various solid freeform fabrication techniques for making three-dimensional articles or objects by selective deposition, jetting, fused deposition modeling, multi-jet modeling, and other additive manufacturing techniques now known in the art or that may be known in the future that use a build material or ink to fabricate three-dimensional objects.

Instructions in the form of schematics encompassing any of the embodiments disclosed herein may be given to a computer to be carried out by a 3D printer. In some embodiments, components of the system may be color coded to signify various properties.

Components of the system may be sterilizable. In various embodiments, one or more components of the system are sterilized by radiation in a terminal sterilization step in the final packaging. Terminal sterilization of a product provides greater assurance of sterility than from processes such as an aseptic process, which require individual product components to be sterilized separately and the final package assembled in a sterile environment.

Typically, in various embodiments, gamma radiation is used in the terminal sterilization step, which involves utilizing ionizing energy from gamma rays that penetrates deeply in the device. Gamma rays are highly effective in killing microorganisms, they leave no residues nor have sufficient energy to impart radioactivity to the device. Gamma rays can be employed when the device is in the package and gamma sterilization does not require high pressures or vacuum conditions, thus, package seals and other components are not stressed. In addition, gamma radiation eliminates the need for permeable packaging materials.

In various embodiments, electron beam (e-beam) radiation may be used to sterilize one or more components of the system. E-beam radiation comprises a form of ionizing energy, which is generally characterized by low penetration and high-dose rates. E-beam irradiation is similar to gamma processing in that it alters various chemical and molecular bonds on contact, including the reproductive cells of microorganisms. Beams produced for e-beam sterilization are concentrated, highly-charged streams of electrons generated by the acceleration and conversion of electricity.

Other methods may also be used to sterilize one or more components of the system, including, but not limited to, gas sterilization, such as, for example, with ethylene oxide or steam sterilization.

In various embodiments, a kit or system is provided that may include additional parts along with the liner combined together to be used with the tray. The kit may include the liner in a first compartment. A second compartment may include the tray. A third compartment may include a cover. A fourth compartment may include an additional cover and/or a lid. A fifth compartment may include a fluid such as a foam detergent. A sixth compartment may include gloves and other procedural supplies for maintaining sterility, as well as an instruction booklet or notification of a website where instructions for using the kit or system can be located. Each component of the system or kit may be separately packaged in a plastic pouch. A cover of the kit may include illustrations of the use of the cover and a clear plastic cover may be placed over the compartments to maintain sterility.

From the foregoing description, one of ordinary skill in the art can easily ascertain the essential characteristics of this disclosure, and without departing from the spirit and scope thereof, can make various changes and modifications to adapt the disclosure to various usages and conditions. The implementations described hereinabove are meant to be illustrative only and should not be taken as limiting of the scope of the disclosure, which is defined in the following claims.

What is claimed is:

1. An endoscope storage system, the system comprising a cover for an endoscope storage tray, the cover comprising a flexibly deformable sheet material substantially impermeable to fluids, the flexibly deformable sheet material configured to be temporarily secured to the endoscope storage tray so as to cover at least an interior of the endoscope storage tray; a liner having an interior comprising a flexibly deformable material substantially impermeable to fluids and an absorbent material disposed within or attached to at least a portion of the flexibly deformable material of the liner, the liner configured to temporarily line at least the interior of the endoscope storage tray; and a detergent container, the detergent container having an outlet configured to dispense detergent to an inlet of the cover, liner and/or endoscope storage tray and to the interior of the endoscope storage tray.

2. The system of claim 1, wherein the system comprises a surface adjacent to the detergent container and/or the inlet, the surface having an actuation button configured to control dispensing of the detergent from the detergent container to the inlet and into the interior of the endoscope storage tray.

3. The system of claim 1, wherein the detergent container has a pressurized foam detergent therein configured to preclean the endoscope stored within the interior of the endoscope storage tray.

4. The system of claim 1, wherein the cover is a sealable bag that extends over the entire endoscope storage tray.

5. The system of claim 1, wherein the detergent is dispensed to an exterior surface of the endoscope and/or interior surfaces of the endoscope.

6. The system of claim 1, wherein the inlet engages one or more channels of the endoscope.

7. The system of claim 1, wherein the inlet comprises a connector having a first port and a second port, the first port configured to dispense the detergent to the exterior of the endoscope, the second port connected to a channel of the endoscope and configured to dispense detergent in the channel of the endoscope.

8. The system of claim 1, wherein the system comprises a cart for storing the endoscope storage tray.

9. The system of claim 1, wherein the liner is disposable and is sterile or non-sterile.

* * * * *